United States Patent [19]

Warren et al.

[11] Patent Number: 5,785,982
[45] Date of Patent: Jul. 28, 1998

[54] DIMETHYL SUBSTITUTED OXYMETHYL CYCLOHEXANE DERIVATIVES FOR THEIR INSECT REPELLENCY PROPERTIES

[75] Inventors: Craig B. Warren, Rumson; Anna B. Marin, Long Branch, both of N.J.; Jerry F. Butler, Gainesville, Fla.; Anubhav P.S. Narula, Hazlet, N.J.

[73] Assignees: International Flavors & Fragrances Inc., New York, N.Y.; The University of Florida, Gainesville, Fla.

[21] Appl. No.: 687,261

[22] Filed: Jul. 25, 1996

Related U.S. Application Data

[60] Division of Ser. No. 496,124, Jun. 27, 1995, Pat. No. 5,576,010, which is a continuation-in-part of Ser. No. 253,244, Jun. 2, 1994, Pat. No. 5,472,701, which is a division of Ser. No. 061,044, May 14, 1993, Pat. No. 5,464,626.

[51] Int. Cl.$^6$ ............................. A01N 25/00; A01N 25/08
[52] U.S. Cl. ..................... 424/408; 514/919; 514/772.3; 514/772.7; 514/729; 514/950
[58] Field of Search ............................ 424/408; 514/419, 514/772.3, 772.7, 950, 729

[56] References Cited

PUBLICATIONS

Buchbauer et al., "Zur Synthese Von Fungizid Wirksamen Isocamphanderivaten: Synthesen In Der Isocamphanreihe, 34. MITT." Manatshefte für Chemie 121, 549–554.

*Primary Examiner*—Jeffrey C. Mullis
*Attorney, Agent, or Firm*—Arthur L. Liberman

[57] ABSTRACT

Described is a method for repelling insects by use of oxymethyl cyclohexane derivatives of the structure

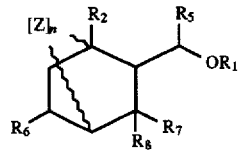

wherein Z is methylene; n is 0 or 1; each of the wavy lines represents a carbon-carbon single bond or no bond; the dashed line represents a carbon-carbon double bond or a carbon-carbon single bond; each of $R_2$, $R_5$, $R_6$, $R_7$ and $R_8$ are the same or different and each represents hydrogen or methyl; and $R_1$ represents hydrogen, acetyl or ethoxycarbonyl with the provisos:

(i) that n is 1 and each of the wavy lines represents a carbon-carbon single bond when $R_1$, $R_2$, and $R_6$, are each hydrogen, $R_5$, $R_7$ and $R_8$ are each methyl and the dashed line is a carbon-carbon single bond;

(ii) n is 0 and each of the wavy lines represents no bond when $R_5$ and $R_7$ are each hydrogen and $R_6$ and $R_8$ are each methyl;

(iii) $R_2$ is methyl only when $R_1$ is ethoxycarbonyl; and (iv) the dashed line is a carbon-carbon single bond only when $R_1$ is hydrogen.

6 Claims, 13 Drawing Sheets

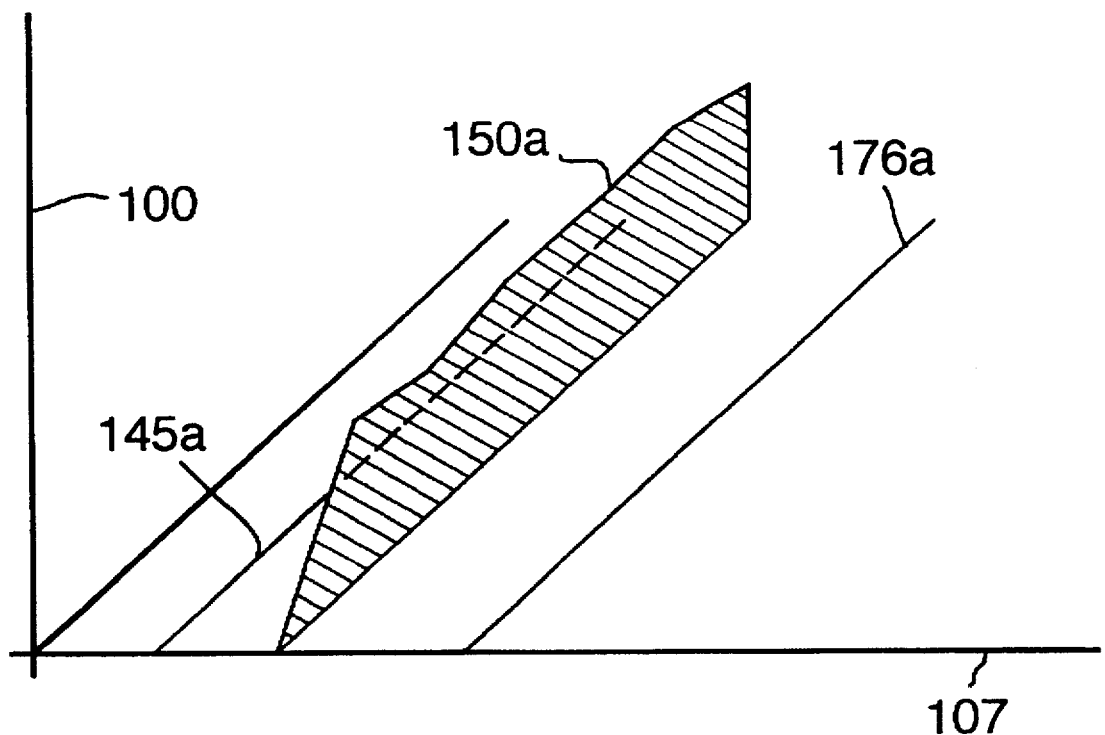
FIG.1-A
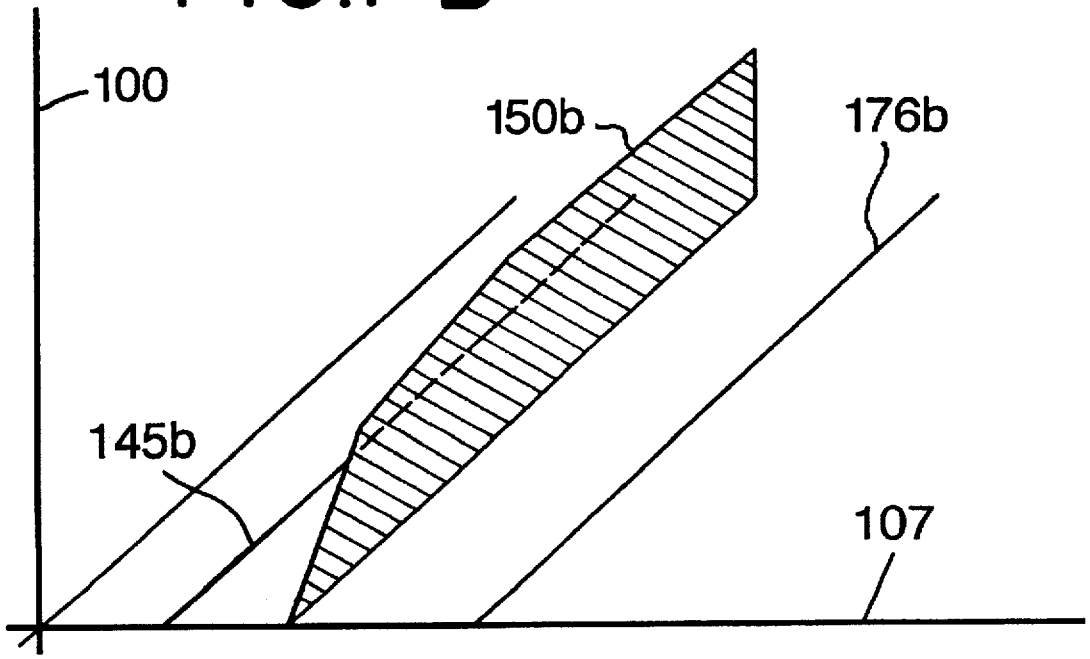
FIG.1-B

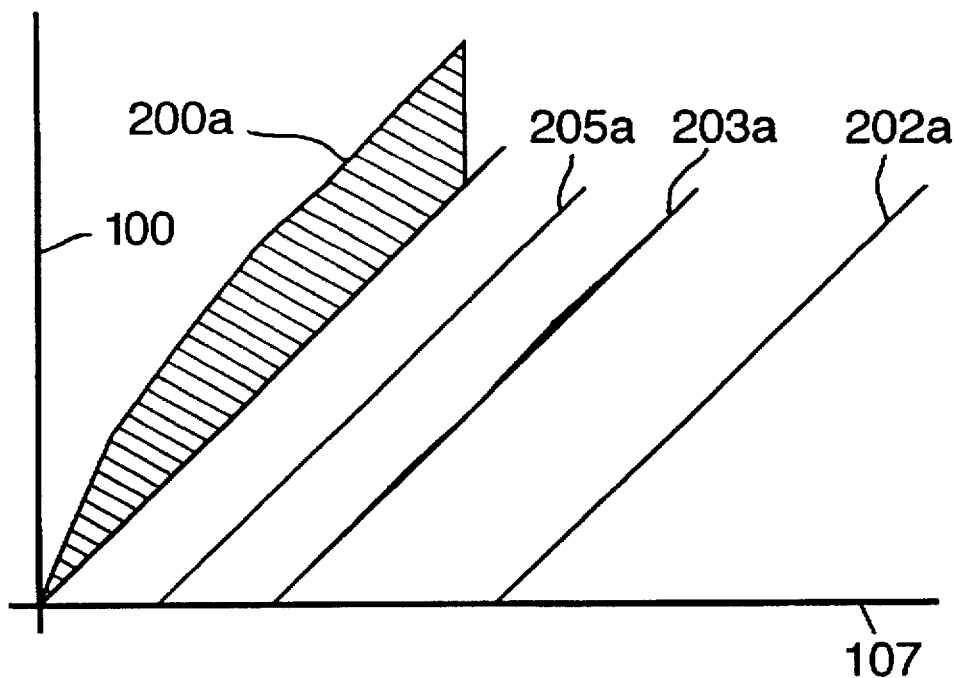
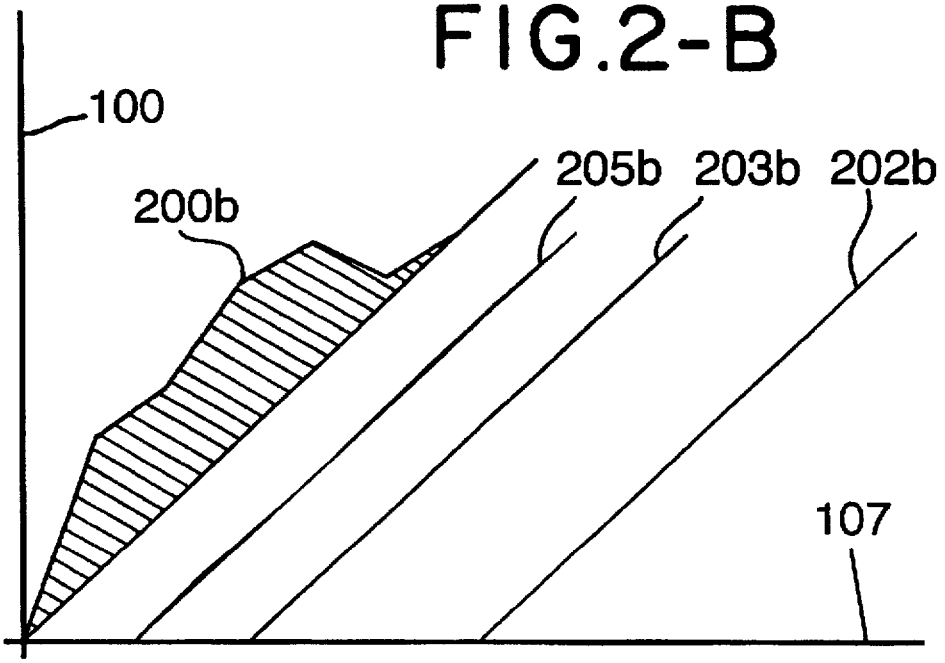

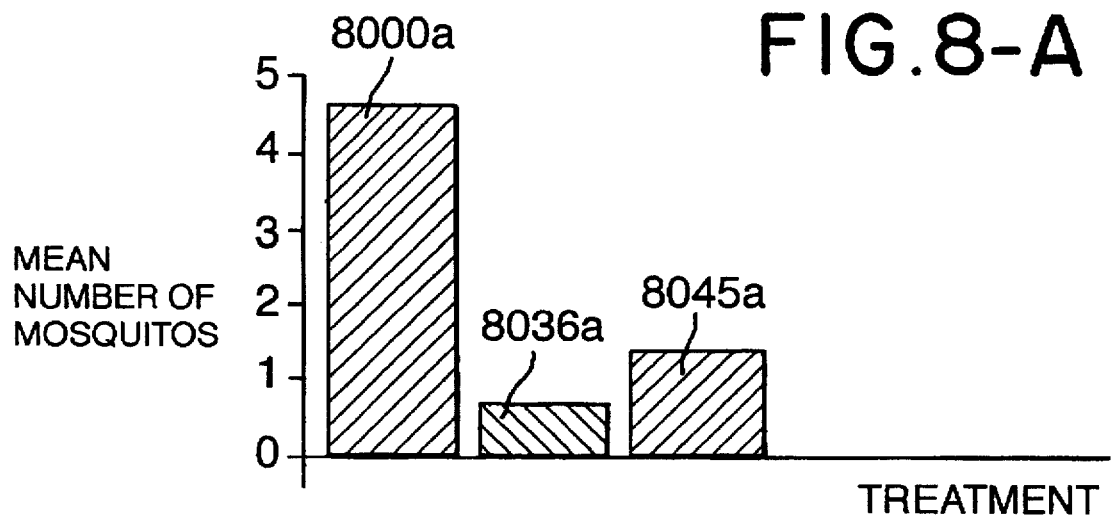
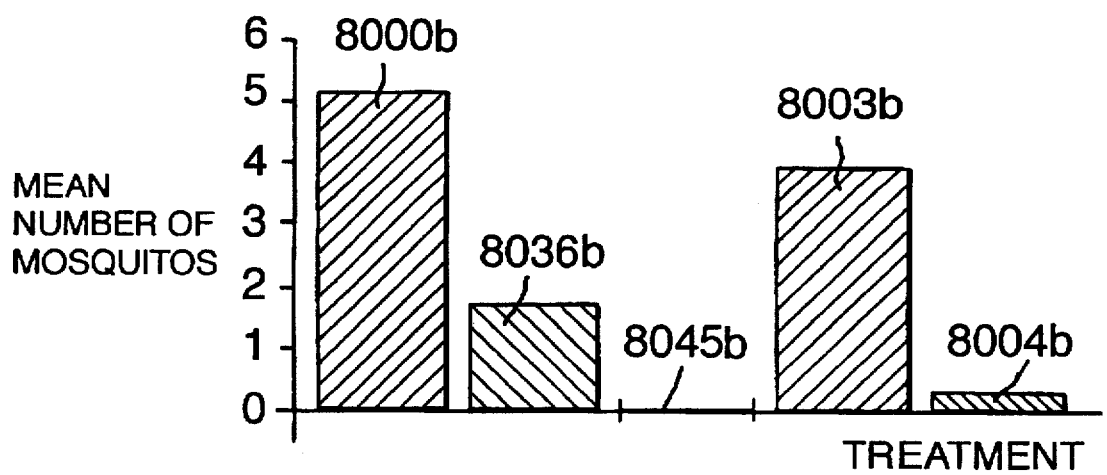

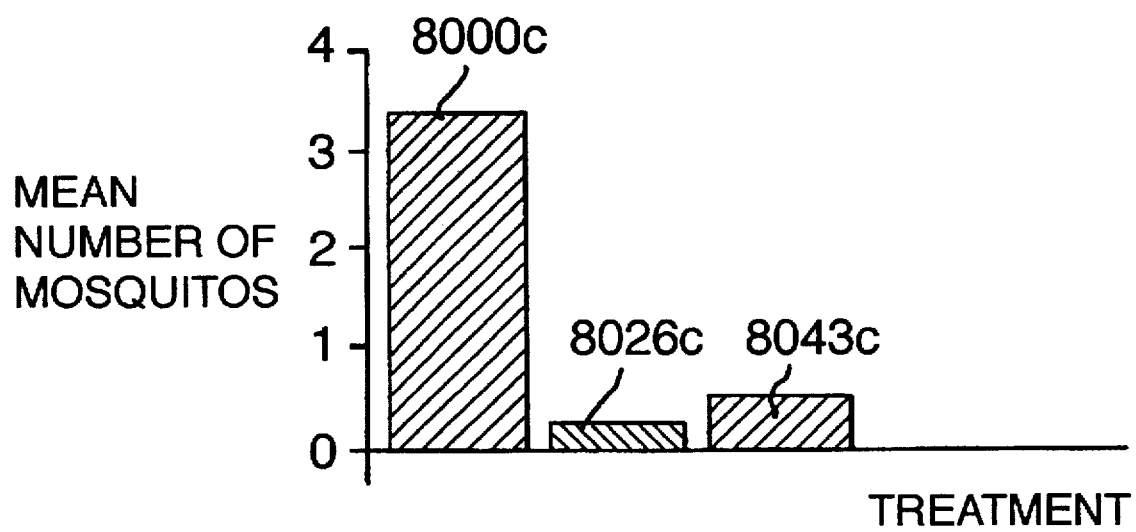
FIG. 8-C

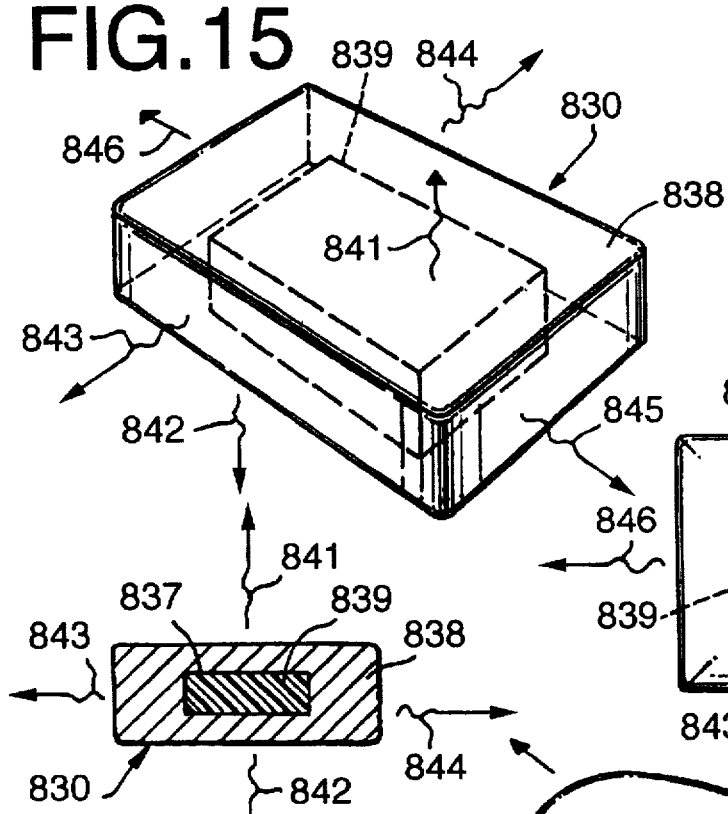
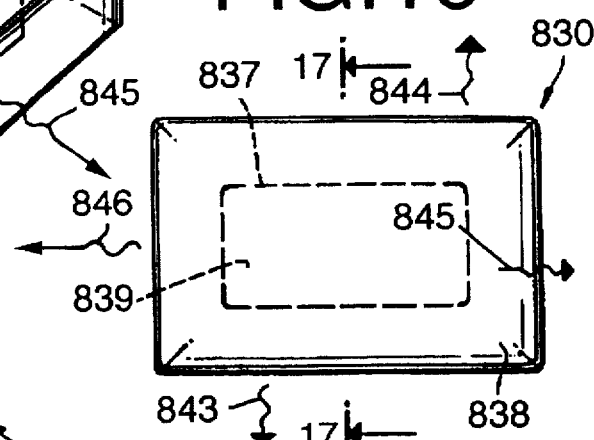
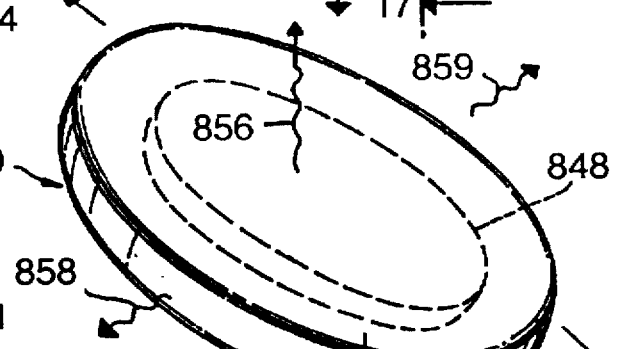
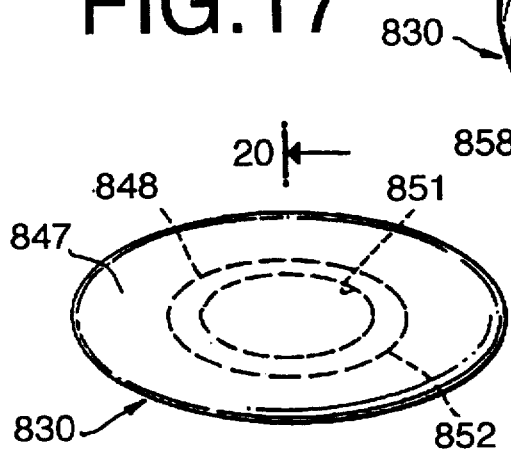
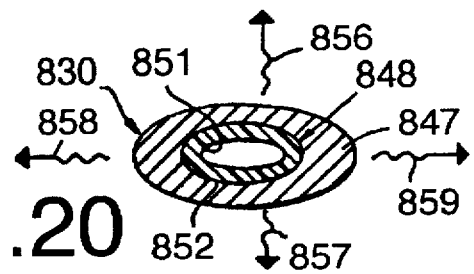

DIMETHYL SUBSTITUTED OXYMETHYL CYCLOHEXANE DERIVATIVES FOR THEIR INSECT REPELLENCY PROPERTIES

RELATED CO-PENDING PATENT APPLICATIONS

This is a Divisional of application Ser. No. 08/496,124, now U.S. Pat. No. 5,576,010, filed on Jun. 27, 1995 which is a Continuation-in-Part of application, Ser. No. 08/253,244 filed on Jun. 2, 1994, now U.S. Pat. No. 5,472,701 issued on Dec. 5, 1995, which, in turn, is a Streamline Divisional of application for U.S. Letters Pat. Ser. No. 08/061,044 filed on May 14, 1993, now U.S. Letters Patent No. 5,464,626 issued on Nov. 7, 1995.

BACKGROUND OF THE INVENTION

This invention relates to the use of dimethyl substituted oxymethyl cyclohexane derivatives defined according to the generic structure:

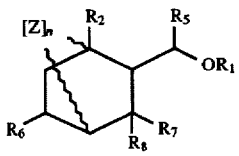

wherein Z is methylene; n is 0 or 1; each of the wavy lines represents a carbon—carbon single bond or no bond; the dashed line represents a carbon—carbon double bond or a carbon—carbon single bond; each of $R_2$, $R_5$, $R_6$, $R_7$ and $R_8$ are the same or different and each represents hydrogen or methyl; and $R_1$ represents hydrogen, acetyl or ethoxycarbonyl with the provisos:

(i) that n is 1 and each of the wavy lines represents a carbon-carbon single bond when $R_1$, $R_2$, and $R_6$, are each hydrogen, $R_5$, $R_7$ and $R_8$ are each methyl and the dashed line is a carbon-carbon single bond;

(ii) n is 0 and each of the wavy lines represents no bond when $R_5$ and $R_7$ are each hydrogen and $R_6$ and $R_8$ are each methyl;

(iii) $R_2$ is methyl only when $R_1$ is ethoxycarbonyl; and (iv) the dashed line is a carbon-carbon single bond only when $R_1$ is hydrogen.

This invention also relates to the use of such compounds and compositions of matter in insect repellent soaps and the like wherein the compositions of matter are used as such or in combination in control release systems with polymers such as biodegradable polymers.

The prior art discloses a vast number of floral type fragrance materials useful in perfumery. However, such floral type materials in many instances are attractants rather than repellents for various insects including the wide variety of mosquitoes which proliferate in temperate, subtropical and tropical zones as well as the wide variety of flies (e.g., Musca domestica L. (Diptera:Muscidae)) which proliferate in the temperate and cooler climate zones.

The dimethyl substituted oxymethyl cyclohexane derivatives of our invention which are repellents have aesthetically pleasing aromas as disclosed, for example, in U.S. Letters Pat. No. 5,098,886 issued Mar. 24, 1992; U.S. Letters Pat. No. 5,100,872 issued on Mar. 31, 1992, U.S. Letters Pat. No. 4,289,146 issued on Sep. 15, 1981; and U.S. Letters Pat. No. 4,321,164 issued on Mar. 23, 1982, the specifications for which are incorporated herein by reference.

BRIEF DESCRIPTION OF THE DRAWINGS

FIG. 1A is a series of graphs depicted in three dimensions (in a rectangular mode for the "X" and "Y" axes) showing the relative attractiveness of repellency of air, FLORALOL having the structure:

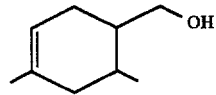

and ISOCYCLOGERANIOL having the structure:

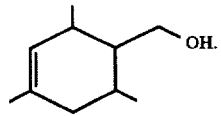

The graphs are based on experiments run for a period of one hour with six intervals of ten minutes each using as the insect to be tested the mosquito, Aedes aegypti. The results are tabulated in Table I(A), infra.

FIG. 1B is a series of graphs depicted in three dimensions (in a rectangular mode for the "X" and "Y" axes) showing the relative attractiveness or repellency of air, FLORALOL having the structure:

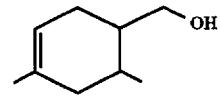

and ISOCYCLOGERANIOL having the structure:

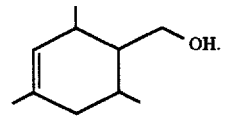

The graphs are based on experiments run for a period of six hours with six intervals of one hour each using as the insect to be tested the mosquito, Aedes aegypti. The results are tabulated in Table I(B), infra.

FIG. 2A is a series of graphs depicted in three dimensions (in /rectangular mode for the "X" and "Y" axes) showing the relative attractiveness or repellency of air, ISOCYCLOGERANIOL having the structure:

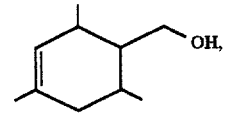

FLORALATE having the structure:

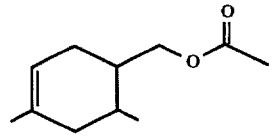

and DIHYDROFLORALOL having the structure:

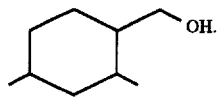

The graphs are based on experiments run for a period of one hour with six intervals of ten minutes each using as the insect to be tested the mosquito, *Aedes aegypti*. The results are tabulated in Table II(A), infra.

FIG. 2B is a series of graphs depicted in three dimensions (in a rectangular mode for the "X" and "Y" axes) showing the relative attractiveness or repellency of air, ISOCYCLOGERANIOL having the structure:

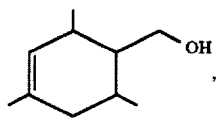

FLORALATE having the structure:

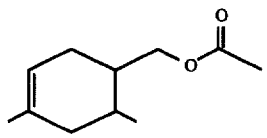

and DIHYDROFLORALOL having the structure:

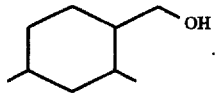

The graphs are based on experiments run for a period of 18 hours with six intervals of 3 hours each using as the insect to be tested the mosquito, *Aedes aegypti*. The results are tabulated in Table II(A), infra.

Figure 3:
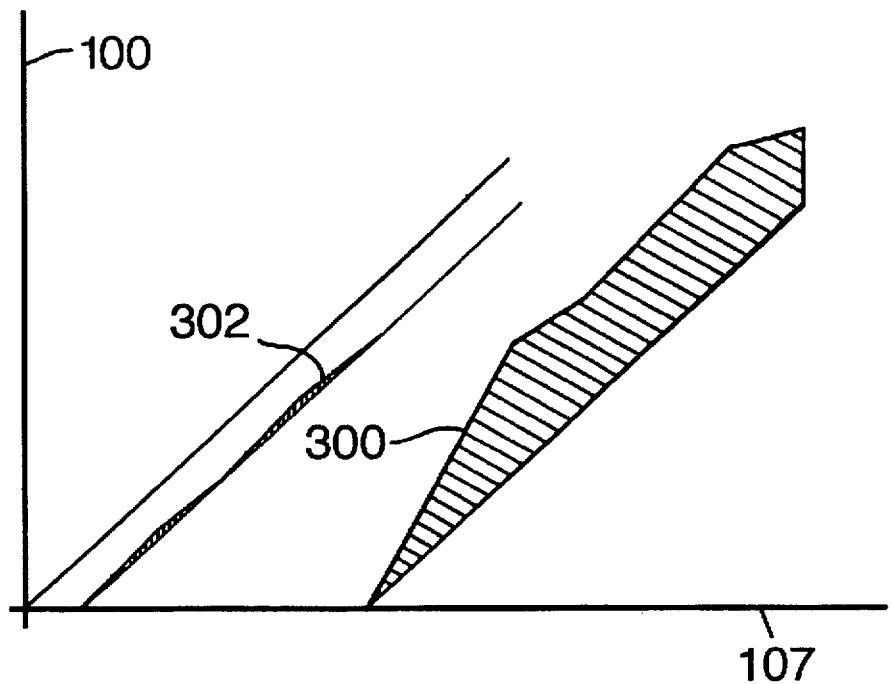

FIG. 3, is a series of graphs depicted in three dimensions (in a rectangular mode for the "X" and "Y" axes) showing the relative attractiveness or repellency of air and DIHYDROFLORALOL having the structure:

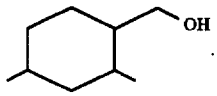

The graphs are based on experiments run for a period of one hour with six intervals of ten minutes each using as the insect to be tested the horn fly, *Haematobia irritans* [L.] The results are tabulated in Table III, infra.

Figure 4:
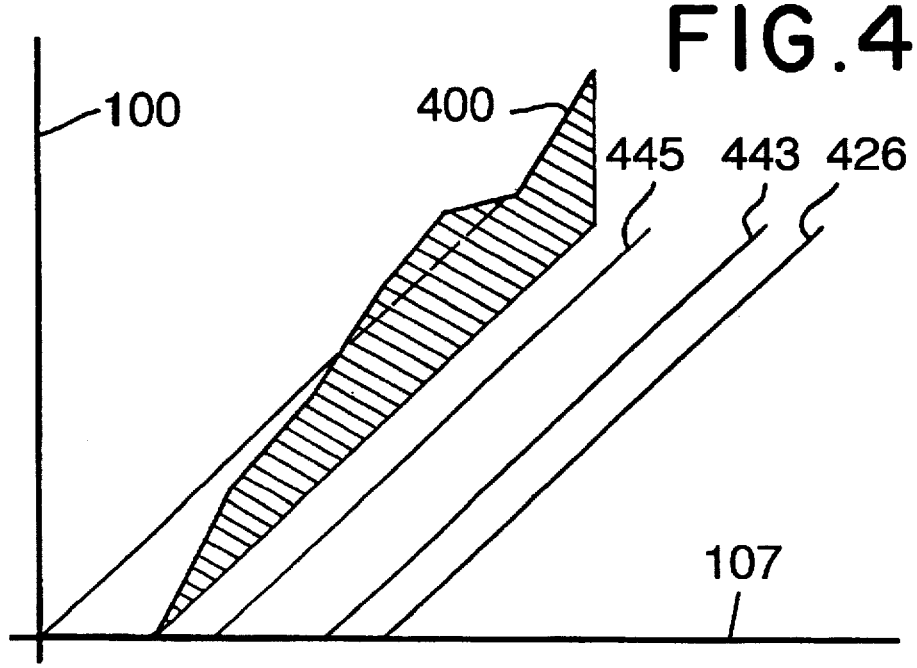

FIG. 4 is a series of graphs depicted in three dimensions (i a rectangular mode for the "X" and "Y" axes) showing the relative attractiveness or repellency of air, ISOCYCLOGERANIOL having the structure:

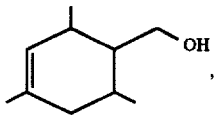

FLORALATE having the structure:

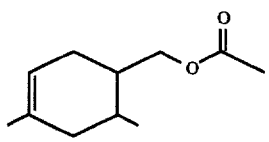

and FLORALOL having the structure:

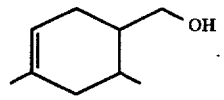

The graphs are based on experiments run for a period of one hour with six intervals of ten minutes each using as the insect to be tested the horn fly, *Haematobia irritans* [L.] The results are, tabulated in Table IV, infra.

Figure 5:
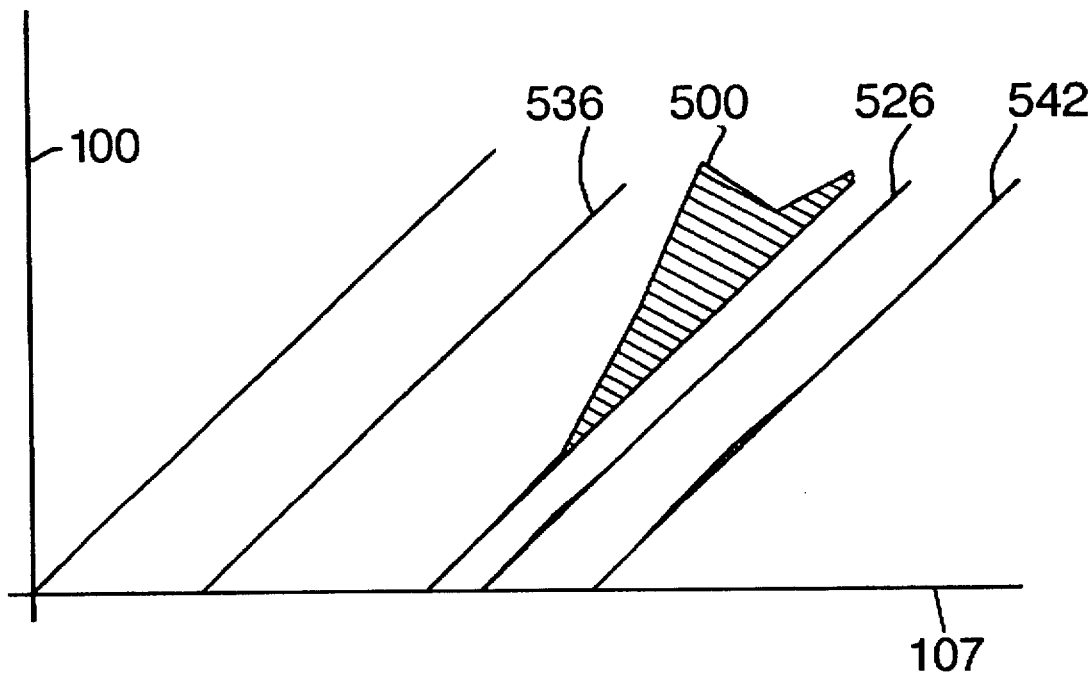

FIG. 5 is a series of graphs depicted in three dimensions (in a rectangular mode for the "X" and "Y" axes) showing the relative attractiveness or repellency of air, CAMEKOL DH having the structure:

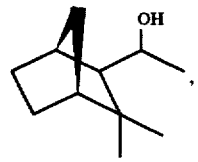

FLORALOL having the structure:

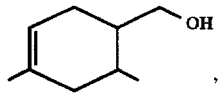

and DIHYDROFLORALOL having the structure:

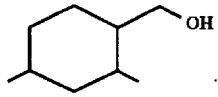

The graphs are based on experiments run for a period of one hour with six intervals of ten minutes each using the insect to be tested the horn fly, *Haematobia irritans* [L.] The results are tabulated in Table V, infra.

Figure 6:
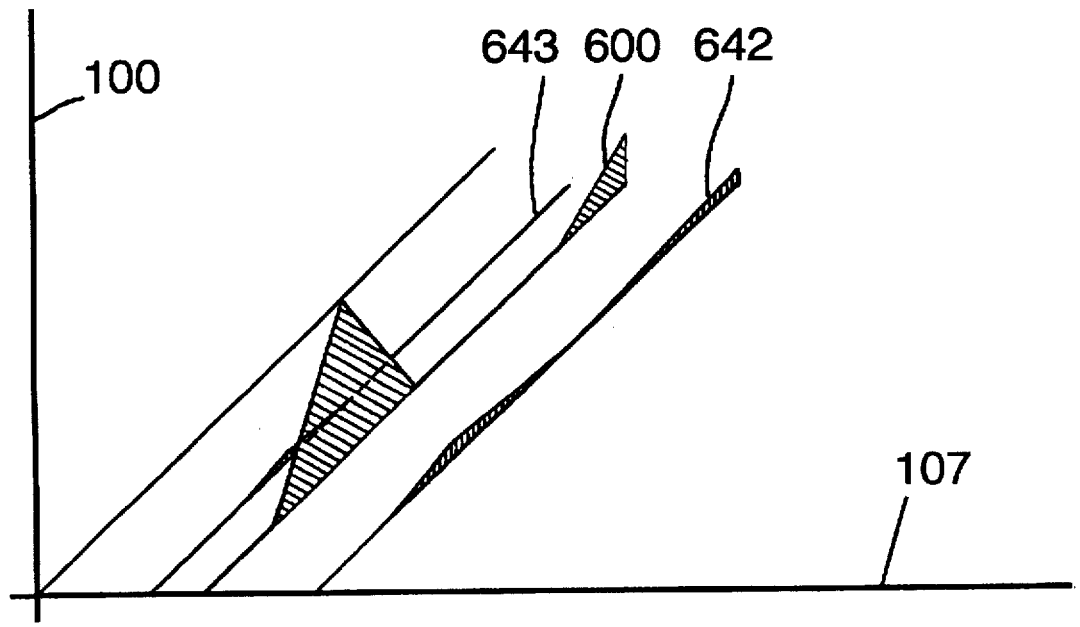

FIG. 6 is a series of graphs depicted in three dimensions (in a rectangular mode for the "X" and "Y" axes) showing the relative attractiveness or repellency of air, FLORALATE having the structure:

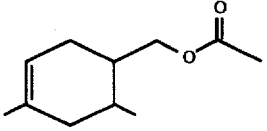

and DIHYDROFLORALOL having the structure:

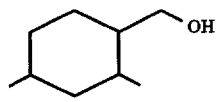

The graphs are based on experiments run for a period of one hour with six intervals of ten minutes each using the insect to be tested the housefly, *Musca domestica L.* (Diptera:Muscidae). The results are tabulated in Table VI, infra.

Figure 7:
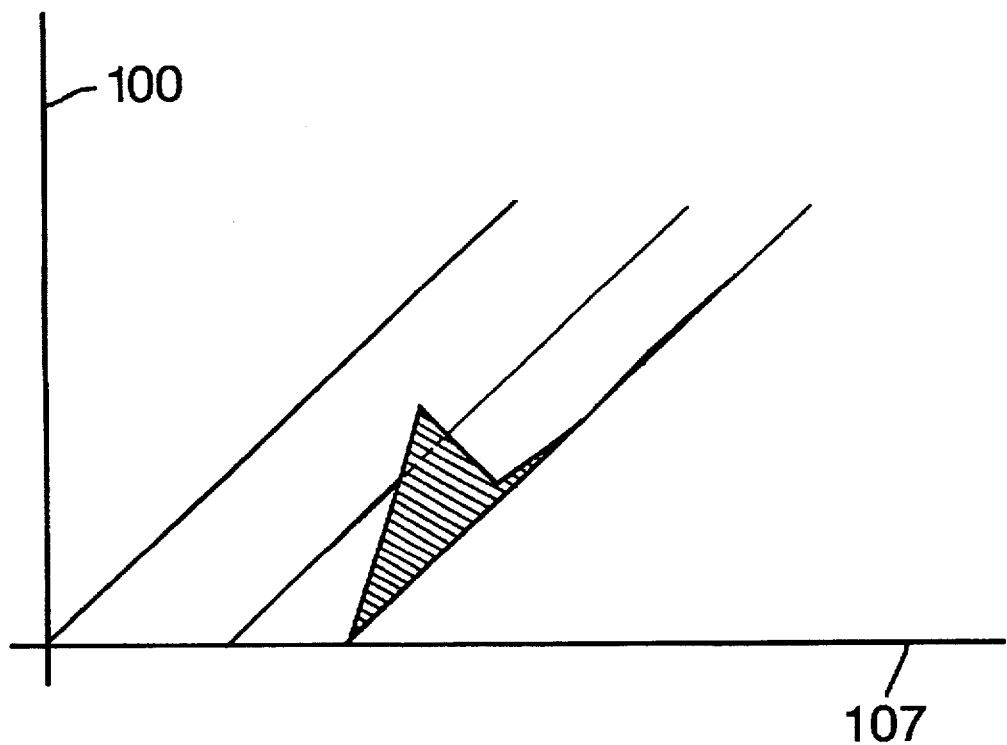

FIG. 7 is a series of graphs depicted in three dimensions (in a rectangular mode for the "X" and "Y" axes) showing the relative attractiveness or repellency of air and FLORALOL having the structure:

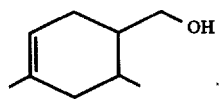

The graphs are based on experiments run for a period of one hour with six intervals of ten minutes each using as the insect to be tested the housefly, *Musca domestics L.* (Diptera:Muscidae). The results are tabulated in Table VII, infra.

Figure 21:
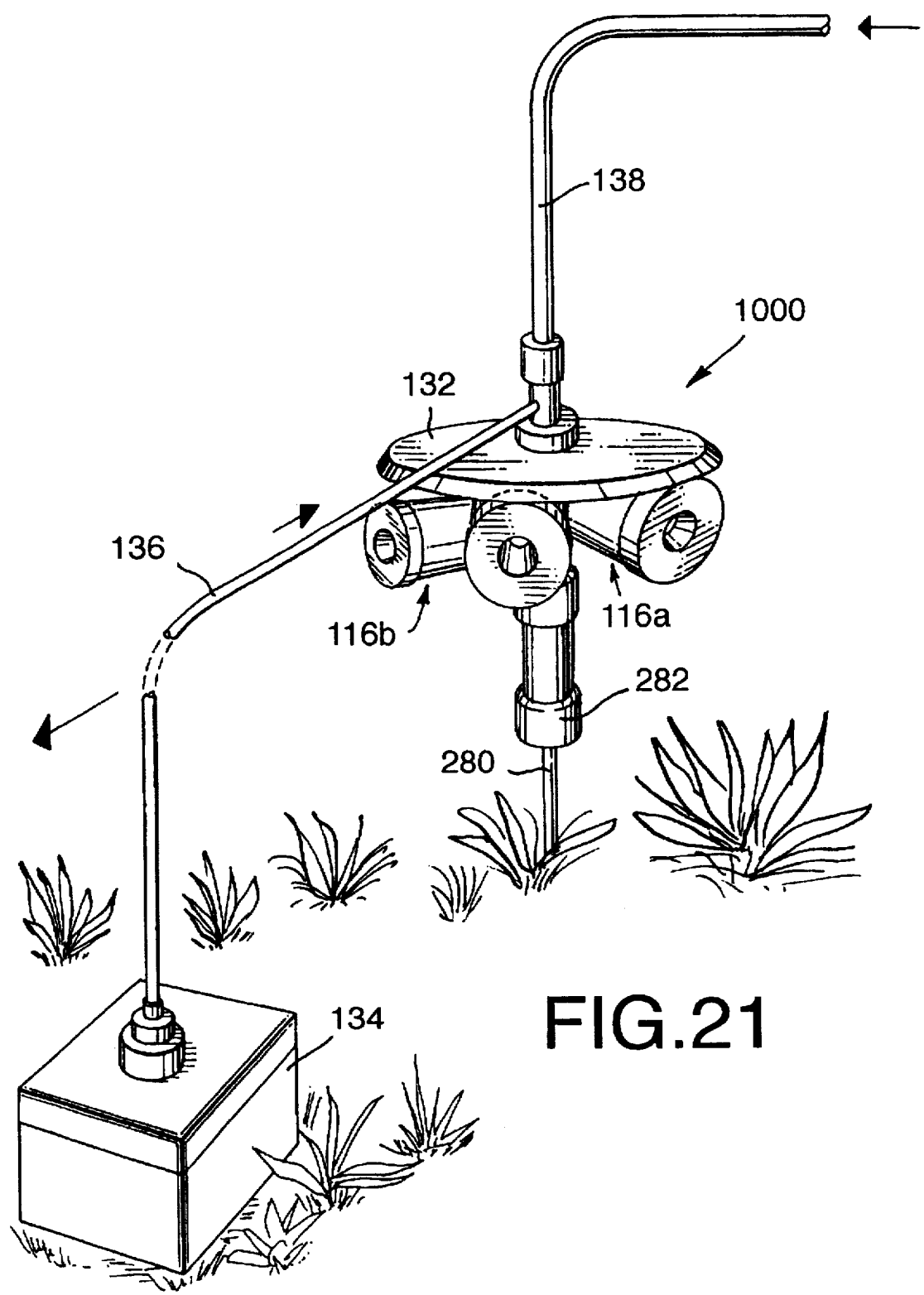

FIG. 8A is a bar graph showing the mean number of insects attracted (on the "Y" axis) versus the treatment substance (on the "X" axis) using the semiochemical field trap of FIG. 21 with six ports and three infrared light emitting diodes, showing treatment with:

(i) a 50:50 mixture of air and $CO_2$;

(ii) CAMEKOL DH having the structure:

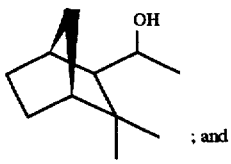

(iii) ISOCYCLOGERANIOL having the structure:

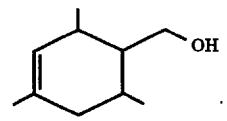

The insects measured using the apparatus of FIG. 21 are as follows:

*Culex nigripalpus;*
*Aedes atlanticus;*
*Culex salinarius;*
*Aedes vexans;*
*Culex spp.;*
*Simulium spp.;*
*Psoroferia ferox;*
*Aedes infirmatus;*
*Drosophila melanogaster;*
*Coccinellidae;*
*Anopheles crucians;*
*Psoroferia columbiae;*
*Culicoides spp.;* and
*Aedes spp.*

FIG. 8B is a bar graph showing the mean number of insects (on the "Y" axis) trapped versus treatment substance (on the "X" axis) using the semiochemical field trap of FIG. 21 having six ports with three infrared light emitting diodes. The treatment substances used are:

(i) a 50:50 mixture of air and $CO_2$;

(ii) DIHYDROFLORALOL having the structure:

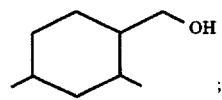

(iii) ISOCYCLOGERANIOL having the structure:

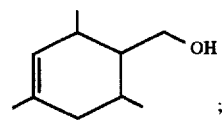

(iv) the compound having the structure:

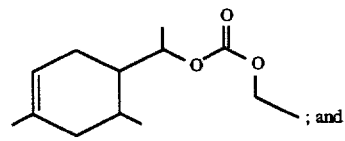
; and (v) the compound having the structure:

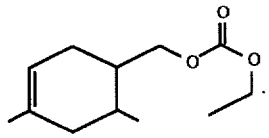
.

The insects measured as to attractiveness or repellency are as follows:

*Culex nigripalpus;*
*Aedes atlanticus;*
*Culex salinarius;*
*Aedes vexans;*
*Culex spp.;*
*Simulium spp.;*
*Psoroferia ferox;*
*Aedes infirmatus;*
*Drosophila melanogaster;*
*Coccinellidae;*
*Anopheles crucians;*
*Psoroferia columbiae;*
*Culicoides spp.;* and
*Aedes spp.*

FIG. 8C is a bar graph showing the mean number of insects attracted (on the "Y" axis) versus treatment substance (on the "X" axis) using the semiochemical field trap of FIG. 21 (described, infra) using treatment substances:

(i) a 50:50 mixture of air and $CO_2$;

(ii) FLORALOL having the structure:

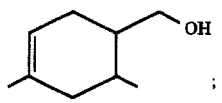

(iii) FLORALATE having the structure:

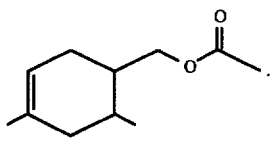

The attractancy or repellency is measured for the following insect species:

Culex nigripalpus;
Aedes atlanticus;
Culex salinarius;
Aedes vexans;
Culex spp.;
Simulium spp.;
Psoroferia ferox;
Aedes infirmatus;
Drosophila melanogaster;
Coccinellidae;
Anopheles crucians;
Psoroferia columbiae;
Culicoides spp.; and
Aedes spp..

Figure 9:
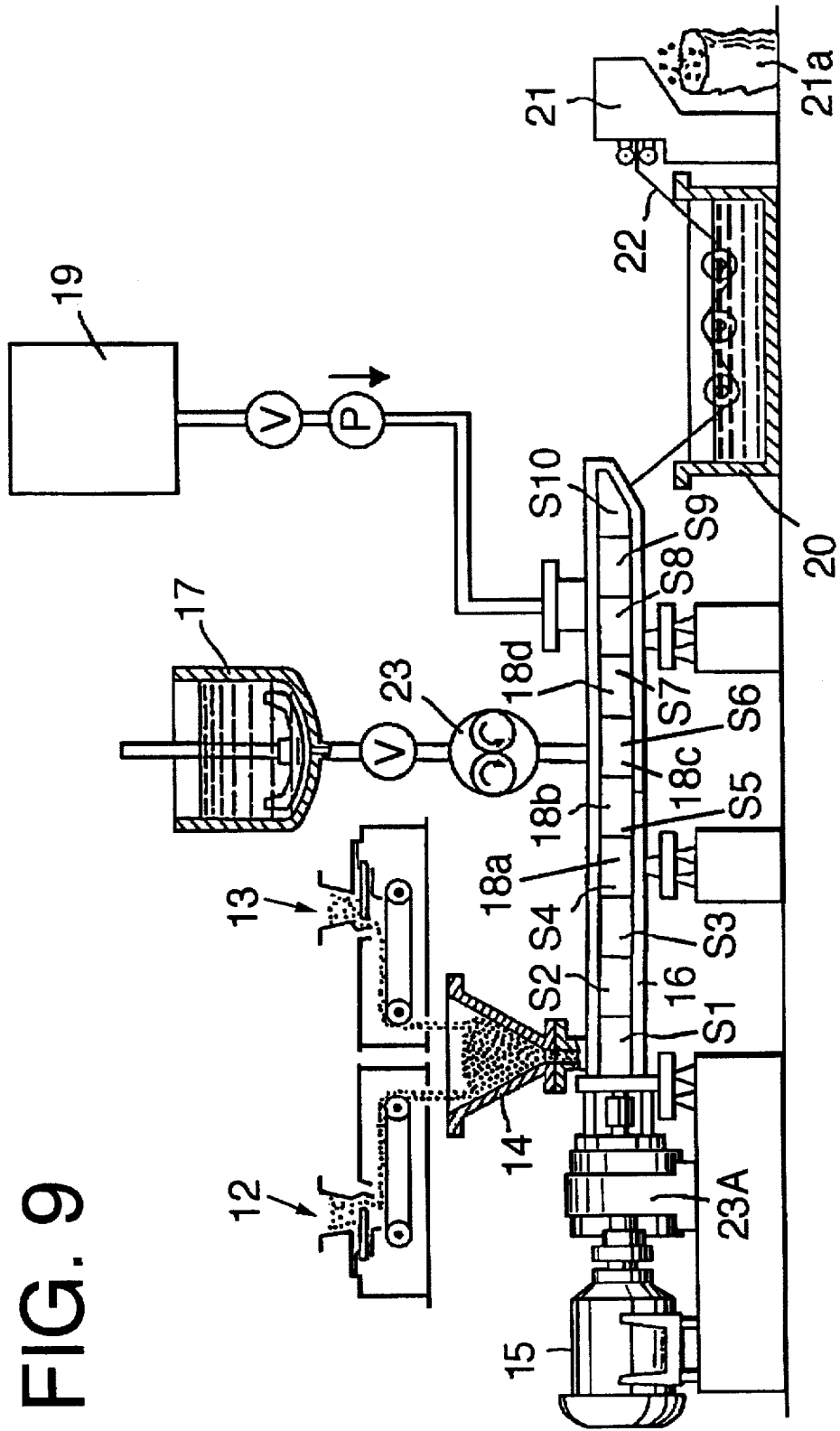

FIG. 9 is a cutaway side elevation schematic diagram of a screw extruder during the compounding of a resin with insect attractants or repellents including the dimethyl substituted oxymethyl cyclohexane derivatives of our invention, while simultaneously adding foaming agent into the hollow portion of the barrel of the extruder and incorporates the pelletizing apparatus used in the pelletizing of the extruded foamed tow product produced as a result of the extrusion operation.

Figure 10:
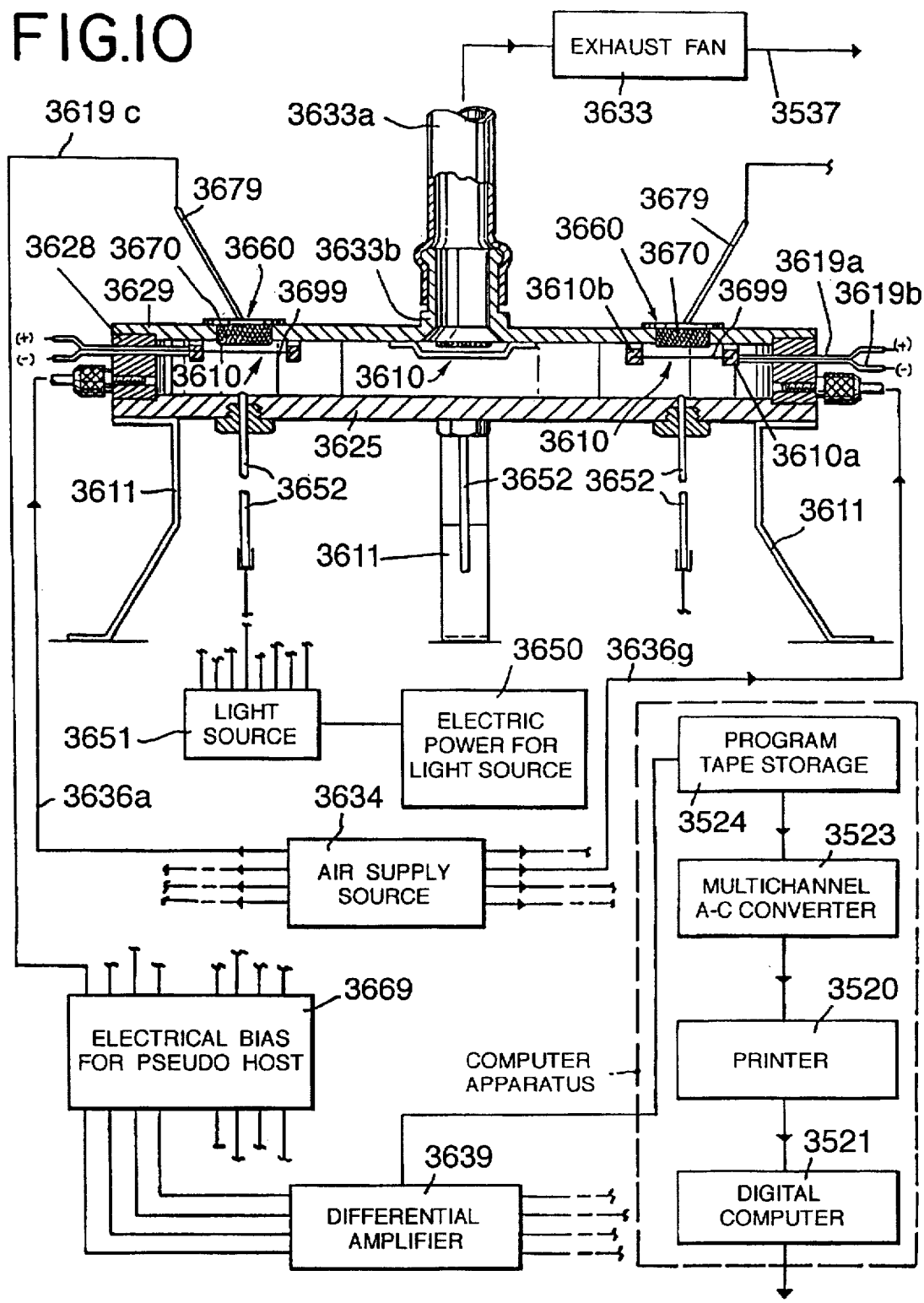

FIG. 10 is a cutaway side elevation view of the base section of the olfactometer apparatus of U.S. Letters Pat. No. 5,134,892 the specification for which is incorporated by reference herein, used in carrying out the testing of the attractants or repellents of our invention indicating in schematic block flow diagram the utilization of computer-assisted efficacy measuring apparatus; but showing only an air supply entry into the side ports of the olfactometer apparatus with the treatment agent being contained in a control release matrix upstream from the air supply source.

Figure 11:
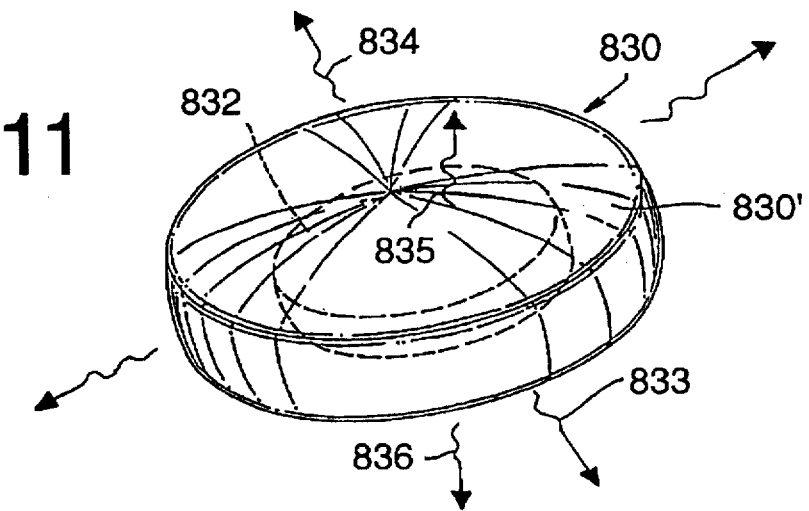

FIG. 11 is a perspective view of an ellipsoidally-shaped detergent tablet containing a solid core which includes fused foamed polymeric particles which contain insect repellents which are one of the repelling dimethyl substituted oxymethyl cyclohexane derivative-containing compositions of our invention and, if desired, also containing an additional polymer, e.g., polyethylene. The polymer particles may, if desired, also contain additional aromatizing agents.

Figure 12:
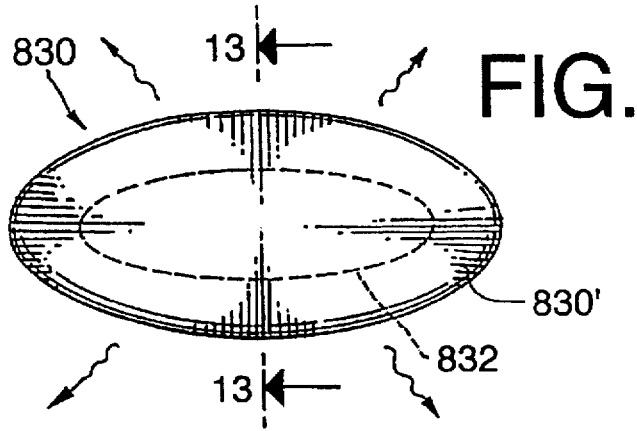

FIG. 12 is the top view of the ellipsoidally-shaped detergent tablet of FIG. 11.

Figure 13:
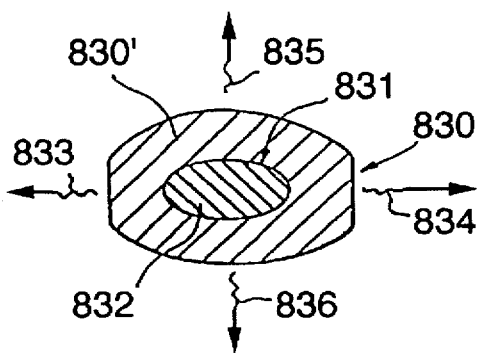

FIG. 13 is a cutaway front view of the ellipsoidally-shaped detergent tablet of FIG. 11 in the direction of the arrows in FIG. 12.

Figure 14:
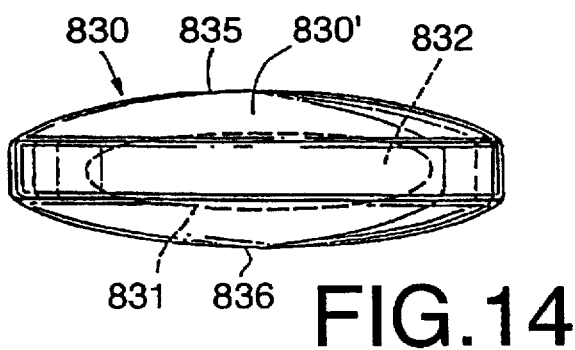

FIG. 14 is a side view of the ellipsoidally-shaped detergent tablet of FIG. 11.

FIG. 15 is a perspective view of a rectangular parallelepiped-shaped detergent tablet containing a rectangular parallelepiped-shaped core comprising a major proportion of fused foamed polymeric particles which contain insect repellents (e.g., one of the repelling dimethyl substituted oxymethyl cyclohexane derivative-containing compositions of our invention) and may or may not be additionally aromatized and, if desired, an additional polymer which may or may not contain insect repellent compositions and which may or may not be additionally aromatized.

FIG. 16 is top view of the rectangular parallelepiped-shaped detergent tablet of FIG. 15.

FIG. 17 is a cutaway front view of the rectangular parallelepiped-shaped tablet of FIG. 15 looking in the direction of the arrows in FIG. 16.

FIG. 18 is a perspective view of an ellipsoidally-shaped detergent tablet containing a hollow insect repellent agent (and, if desired, an additional aromatizing agent) containing core which includes fused foamed polymeric particles containing insect repellent and, if desired, additional aromatizing agent or, in the alternative, a hollow core of fused foamed polymer wherein the insect repellent which is also an aroma imparting agent (and, if desired, an additional aroma imparting agent) is in the solid polymer and not in the void of the plastic core.

FIG. 19 is a top view of the ellipsoidally-shaped detergent tablet of FIG. 18. FIG. 20 is a front cutaway view of the ellipsoidally-shaped detergent tablet of FIG. 18 looking in the direction of the arrows in FIG. 19, the core thereof being hollow and either containing an insect repellent material of our invention (and, if desired, an additional aroma imparting liquid) or, in the alternative, being a hollow core wherein the insect repellent material of our invention (and, if desired, the additional aroma imparting material) is in the solid fused foamed polymeric particles which make up the core and wherein the void does not contain anything.

FIG. 21 is a perspective view of the semiochemical field trap for testing the attractiveness or repellency for blood feeding arthropods using the dimethyl substituted oxymethyl cyclohexane derivative-containing repellency composition of our invention or the attractant of our invention which is the compound having the structure:

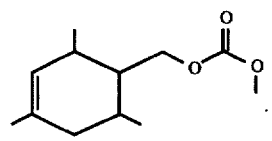

The semiochemical field trap is described in detail in U.S. Letters Pat. No. 5,228,233 issued on Jul. 20, 1993 the specification for which is incorporated herein by reference.

Figure 22:
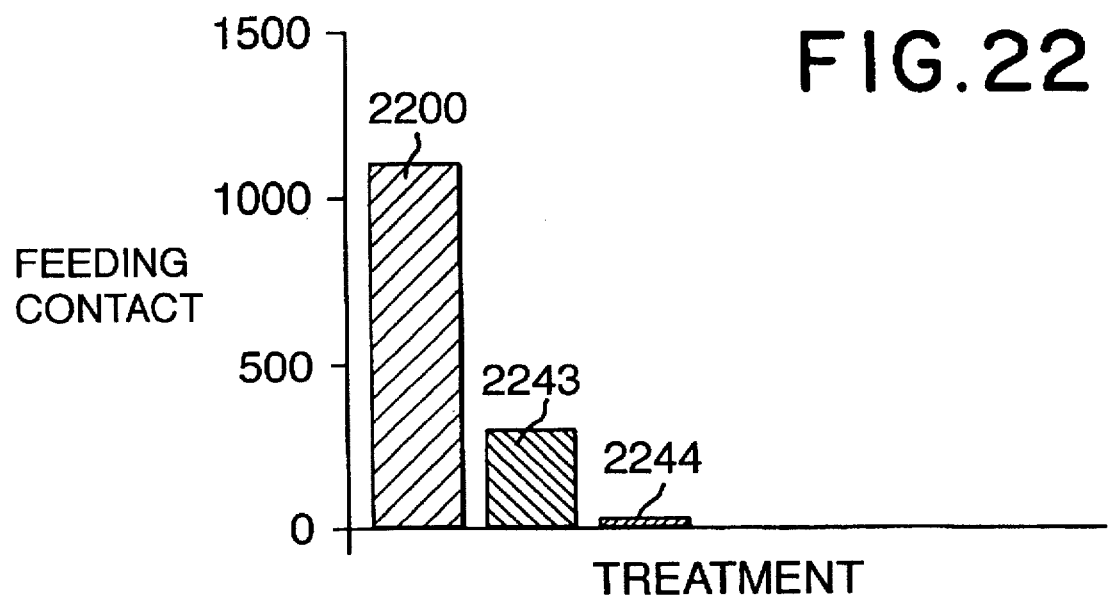

FIG. 22 is a bar graph showing the mean number of feeding contacts (on the "Y" axis) versus the particular treatment substance (on the "X" axis) for air, FLORALATE having the structure:

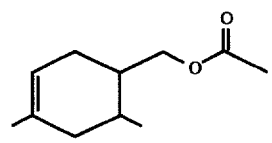

and geranial having the structure:

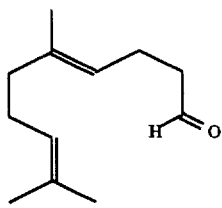

for a mean feeding contact time of one hour.

Figure 23:
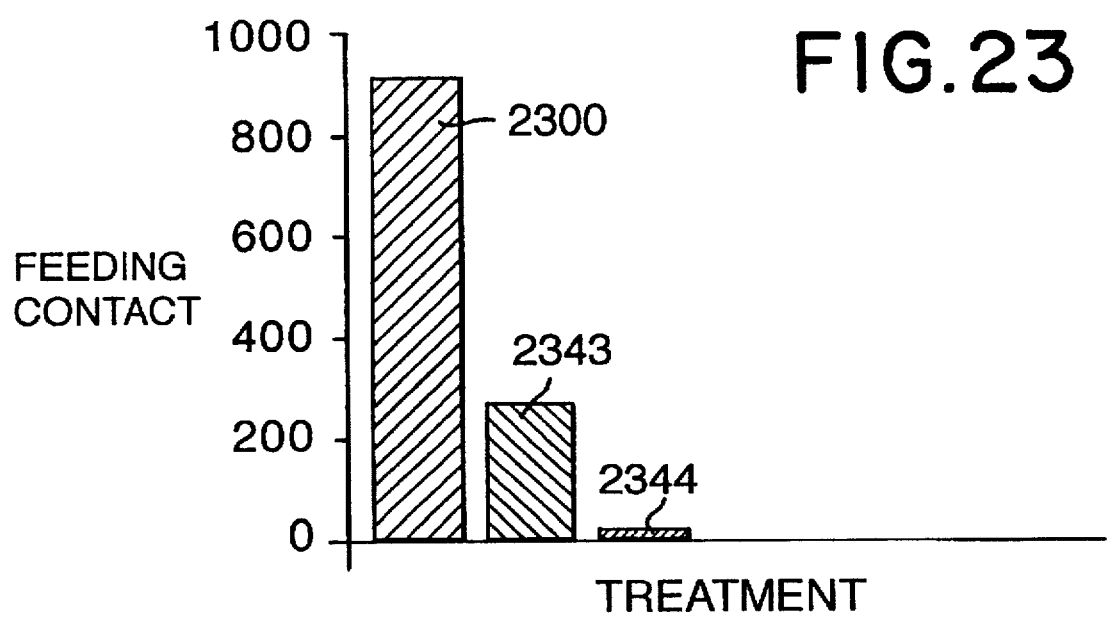

FIG. 23 is a bar graph showing the mean number of feeding contacts (on the "Y" axis) versus the particular treatment substance (on the "X" axis) for air, FLORALATE having the structure:

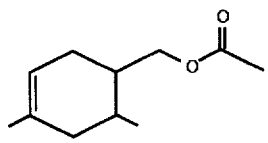

and geranial having the structure:

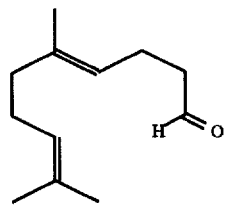

for a mean 2–6 hour feeding contact time.

SUMMARY OF THE INVENTION

This invention relates to the use of dimethyl substituted oxymethyl cyclohexane derivatives defined according to the structure:

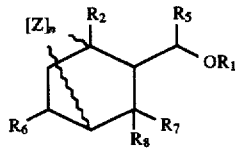

wherein Z is methylene; n is 0 or 1; each of the wavy lines represents a carbon-carbon single bond or no bond; the dashed line represents a carbon-carbon double bond or a carbon-carbon single bond; each of $R_2$, $R_5$, $R_6$, $R_7$ and $R_8$ are the same or different and each represents hydrogen or methyl; and $R_1$ represents hydrogen, acetyl or ethoxycarbonyl with the provisos:

(i) that n is 1 and each of the wavy lines represents a carbon-carbon single bond when $R_1$, $R_2$, and $R_6$ are each hydrogen, $R_5$, $R_7$ and $R_8$ are each methyl and the dashed line is a carbon—carbon single bond;

(ii) n is 0 and each of the wavy lines represents no bond when $R_5$ and $R_7$ are each hydrogen and $R_6$ and $R_8$ are each methyl;

(iii) $R_2$ is methyl only when $R_1$ is ethoxycarbonyl; and (iv) the dashed line is a carbon–carbon single bond only when $R_1$ is hydrogen as insect repellents against houseflies (*Musca domestica L.* (Diptera:Muscidae)), mosquitoes including those set forth on the following species list:

*Culex nigripalpus;*
*Aedes atlanticus;*
*Culex salinarius;*
*Aedes vexans;*
*Culex spp.;*
*Simulium spp.;*
*Psoroferia ferox;*
*Aedes infirmatus;*
*Drosophila melanogaster;*
*Coccinellidae;*
*Anopheles crucians;*
*Psoroferia columbiae;*
*Culicoides spp.;* and
*Aedes spp.* and the horn fly, *Haematobia irritans* [L.].

Specific examples of the dimethyl substituted oxymethyl cyclohexane derivatives useful in the practice of our invention are those having the following structures:

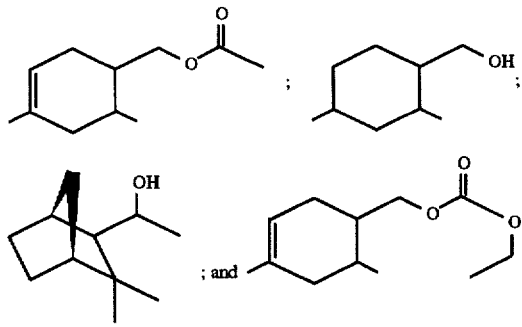

Our invention also relates to the use of the foregoing insect repellent compositions in personal soap compositions, for example, the insect repellent soap composition described in U.S. Letters Pat. No. 4,707,496 issued on Nov. 17, 1987 the specification for which is incorporated by reference herein. Thus, in applying the teachings of U.S. Letters Pat. No. 4,707,496 to our invention, a topical insect repellent soap composition and a method of protection using such a composition is described where the insect repellent soap composition comprises:

(i) from 63.0 up to 99.5% by weight of a soap mixture containing from 4.1 up to 7% by weight of a soap of caprylic acid, from 3.8 up to 7% of a soap of capric acid, from 32.1 up to 45% of a soap of lauric acid, from 12 up to 17.5% by weight of a soap of myristic acid, from 5.0 up to 10% by weight of a soap of palmitic acid, from 1.6 up to 3% by weight of a soap of stearic acid, from 3.5 up to 5% by weight of a soap of oleic acid and from 0.9 up to 5% by weight of a soap of linoleic acid;

(ii) from 0.1 up to 2% by weight of $C_8$–$C_{18}$ straight chain fatty acids;

(iii) from 10 up to 30% by weight of one of the dimethyl substituted oxymethyl cyclohexane derivative-containing compositions of our invention as set forth, supra; and (iv) from 0.2 up to 5% by weight of an effective residual insecticide as described in U.S. Letters Pat. No. 4,707, 496.

Other insect repellent soaps can be produced by adding an appropriate dimethyl substituted oxymethyl cyclohexane derivative-containing composition of our invention to one or more of the compositions described and claimed in U.S. Letters Pat. No. 4,453,909 issued on Jun. 12, 1984 and U.S. Letters Pat. No. 4,438,010 the specifications for which are incorporated by reference herein. Described in said U.S. Letters Pat. No. 4,453,909 and U.S. Letters Pat. No. 4,438, 010 is a process for making a tablet of soap containing a perfume-containing core, hollow or solid fabricated from a hard plastic material either thermosetting or thermoplastic. The soap from the resulting composite tablet is usable until the core is washed clean and contains functional ingredients, e.g., the repellents described, supra, and, optionally, an aromatizing agent until the core is washed clean. This obviates the wastage of soap which normally occurs as a conventional soap tablet becomes very thin on use and at the same time gives rise to a continuously functional ingredient containing soap (e.g., a repellent and optionally aromatizing agent) tablet. Thus, this invention also relates to detergent bars having a plastic core containing an appropriate dimethyl substituted oxymethyl cyclohexane derivative-containing composition and, optionally, an additional perfume. More particularly, this invention relates to detergent bars intended for conventional toilet soap uses either as hand soaps or bath or shower soaps which are elastic or inelastic in nature but which contain a solid plastic core containing insect repellent and, optionally, perfume, giving them unique properties which alleviate wastage thereof and causes the environment surrounding the soap on use thereof to be both insect repellent and, optionally, aromatized in an aesthetically pleasing manner.

Yet another aspect of our invention relates to the use of the dimethyl substituted oxymethyl cyclohexane derivative-containing repellents of our invention taken further in combination with N-(methyl toluyl)-methylpiperidines defined according to the structure:

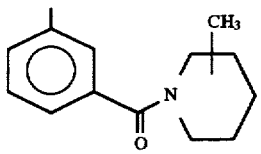

as described in U.S. Letters Pat. No. 3,463,855 issued on Aug. 26, 1969 the specification for which is incorporated by reference herein. The compounds defined according to the structure:

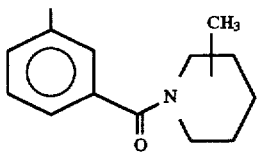

include:

N-(meta-toluyl)-2-methylpiperidine;

N-(meta-toluyl)-3-methylpiperidine; and

N-(meta-toluyl)-4-methylpiperidine.

The proportions of compounds defined according to the structure:

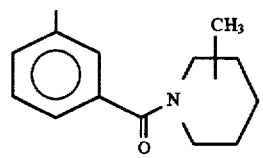

to the appropriate dimethyl substituted oxymethyl cyclohexane derivative-containing composition described, supra, are between 1 part N-(meta-toluyl) methylpiperidine:99 parts appropriate dimethyl substituted oxymethyl cyclohexane derivative-containing composition of our invention down to 99 parts appropriate dimethyl substituted oxymethyl cyclohexane derivative-containing composition of our invention:1 part N-(meta-toluyl)-methylpiperidines.

In addition, the compositions of our invention useful in repelling insects can also contain 1-nonen-3-ol described and claimed in U.S. Letters Pat. Nos. 4,693,890 and 4,759, 228 issued on Jul. 26, 1988 the specifications for which are incorporated by reference herein. The ratio of 1-nonen-3-ol:appropriate dimethyl substituted oxymethyl cyclohexane derivative-containing composition of our invention useful in repellent compositions may vary from about 1 part 1-nonen-3-ol:99 parts appropriate dimethyl substituted oxymethyl cyclohexane derivative-containing composition of our invention down to 99 parts 1-nonen-3-ol:1 parts appropriate dimethyl substituted oxymethyl cyclohexane derivative-containing composition of our invention.

In addition to the soap fabrication, another aspect of our invention relates to the formation of repelling articles containing the appropriate dimethyl; substituted oxymethyl cyclohexane derivative-containing compositions of our invention, that is, articles useful for repelling houseflies (*Musca domestica* L. (Diptera:Muscidae)) or the mosquitoes (Aedes aegypti) or other insect species:

*Culex nigripalpus;*

*Aedes atlanticus;*

*Culex salinarius;*

*Aedes vexans;*

*Culex spp.;*

*Simulium spp.;*

*Psoroferia ferox;*

*Aedes infirmatus;*

*Drosophila melanogaster;*

*Coccinellidae;*

*Anopheles crucians;*

*Psoroferia columbiae;*

*Culicoides spp.;* and

*Aedes spp.* or the horn fly (*Haematobia irritans* [L.]) in combination with compatible polymers which may or may not be biodegradable (for example, high density polyethylene or low density polyethylene, or biodegradable polymers such as biodegradable thermoplastic polyurethanes as disclosed in Japan Kokai Tokyo Koho 92/13710 (abstracted at *Chemical Abstracts*, Volume 116:236397z), biodegradable ethylene polymers having ester linkages in the main chain such as that disclosed by Japan Kokai Tokyo Koho 92/50224 (abstracted at *Chemical Abstracts*, Volume 116:126397z); biodegradable ethylene polymers disclosed by Japan Kokai Tokyo Koho 92/50225 (abstracted at *Chemical Abstracts*, Volume 116:126398a; and poly(epsilon caprolactone) homopolymers and compositions containing same as disclosed in U.S. Letter Pat. Nos. 4,496,467; Nos. 4,469,613 and 4,548,764 the specifications for which are incorporated herein by reference. Thus, another aspect of our invention provides a process for forming appropriate dimethyl substituted oxymethyl cyclohexane derivative-containing compositions containing polymeric particles such as foamed polymeric pellets which include a relatively high concentration of the appropriate dimethyl substituted oxymethyl cyclohexane derivative-containing compositions of our invention as defined, supra.

Thus, another aspect of our invention relates to the formation of appropriate dimethyl substituted oxymethyl cyclohexane derivative-containing polymeric pellets by means of introduction into a single or twin screw extruder, in series, a thermoplastic polymer followed by the appropriate dimethyl substituted oxymethyl cyclohexane derivative-containing composition of our invention which is compatible with the thermoplastic polymer, in turn (optionally), followed by introduction of a gaseous blowing agent or blowing agent which will produce a gas which is inert to the polymer and to the appropriate dimethyl substituted oxymethyl cyclohexane derivative-containing composition previously introduced into the extruder.

The advantage of using a foamed polymeric particle are multiple, to wit:

(i) improved handling;
(ii) greater retention of the appropriate dimethyl substituted oxymethyl cyclohexane derivative-containing composition when not in use; and
(iii) greater length of time during which the release of the appropriate dimethyl substituted oxymethyl cyclohexane derivative-containing composition of our invention from the polymer is at "steady state" or "0 order".

The nature of the extruder utilized in the process of our invention to form the appropriate dimethyl substituted oxymethyl cyclohexane derivative-containing composition-containing polymer particles of our invention may be either single screw or double screw. Thus, the types of extruder that can be used are disclosed at pages 246–267 and 332–349 of the Modern Plastics Encyclopedia, 1982–1983, published by the McGraw-Hill Publishing Company, the disclosure of which is incorporated by reference herein. More specifically, examples of extruders which are usable in carrying out one or more of the processes of our invention (with modification for introduction of the appropriate dimethyl substituted oxymethyl cyclohexane derivative-containing compositions of our invention) downstream from the introduction of the polymer and with further modification that the gaseous blowing agent is introduced still further downstream from the point of introduction of the appropriate dimethyl substituted oxymethyl cyclohexane derivative-containing compositions of our invention are as follows:

1. The Welex "Super Twinch" 3.5 inch extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Wichita, Kans. 67277;
3. Modified Sterling Model 4000 and 5000 series extruder manufactured by Sterling Extruder Corporation of 901 Durham Avenue, South Plainfield, N.J.;
4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Route 206 South, Somerville, N.J. 08876;
6. The ZSK Twin Screw Co-Rotating Extruder manufactured by the Werner & Pfleiderer Corporation of 663 East Crescent Avenue, Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 48601; and
9. The Berstorff single screw, twin screw or foam extrusion equipment manufactured by Berstorff Corporation, P.O. Box 240357, 8200-A Arrowing Boulevard, Charlotte, N.C. 28224.

In producing the appropriate dimethyl substituted oxymethyl cyclohexane derivative-containing composition-containing polymer particles of our invention, various polymers may be utilized, for example, low density polyethylene, high density polyethylene, polypropylene, the copolymer of ethylene and vinyl acetate, and polyvinyl chloride. More specifically, the polymers used in the practice of our invention may be copolymers of ethylene and a polar vinyl monomer selected from (a) vinyl acetate; (b) ethyl acrylate; (c) methyl acrylate; (d) butyl acrylate; and (e) acrylic acid including the hydrolyzed copolymer of ethylene and vinyl acetate. Preferred copolymers are ethylene/vinyl acetate with about 9 to 60% vinyl acetate and ethylene/ethyl acrylate with about 6 to 18% ethyl acrylate.

Resins of the type disclosed for use as copolymers are commercially available in the molding powder form; for example, ethylene vinyl acetate copolymers are marketed by the E.I. duPont Nemours Company under the Tradename ELVAX® and by the Arco Polymer Division under the Trademark DYLAND® and by the Exxon Corporation of Linden, New Jersey under the Trademark DEXXON®. Ethylene/ethyl acrylate copolymers are marketed by Union Carbide Corporation under the Trademark EEA RESIN®.

The polymer is added to the single screw or twin screw extruder at a feed rate in the range of from about 80 up to about 300 pounds per hour while maintaining the temperature of the screw extruder between about 160° C. and about 240° C. If the polymer or copolymer powder is added to the extruder at a reference "barrel segment", then the appropriate dimethyl substituted oxymethyl cyclohexane derivative-containing composition of our invention is added to the extruder under pressure downstream from the retention point of the polymer at one or more of the "barrel segments" (S-2, S-3, S-5, S-6, S-7, S-8 or S-9) (referring to FIG. 9 briefly described, supra, and described in detail, infra).

The proportion of the appropriate dimethyl substituted oxymethyl cyclohexane derivative-containing composition (taken further together with other insect repelling materials, if desired) to resin can vary from small but effective amounts on the order of about 1% of the weight of the resin body up to about 45% by weight of the resin body. In general, it is preferred to use between about 5% up to about 30% based on the weight of the resin body of insect repellent composition of our invention. This is an optimum amount balancing the proportion of the insect repellent composition of our invention against the time period over which the article emits the insect repellent composition and against the tendency of the components of the insect repellent composition to oil out either individually or in combination. This "oiling out" is specifically avoided as a result of the use of the foaming agent discussed, infra.

Various polymers are useful in the practice of our invention. Specific examples of polymers useful in the practice of our invention are as follows:

(a) DYLAN® brand of low density polyethylene. DYLAN® is a trademark owned by the Atlantic Richfield Company of Los Angeles, Calif.;

(b) DYLITE® ( of expandable polystyrene composition. DYLITE® is a trademark of the Atlantic Richfield Company of Los Angeles, Calif.;

(c) SUPER DYLAN® is a trademark of the Atlantic Richfield Company of Los Angeles, Calif.;

(d) blended polyethylene and carbon black as specifically taught in U.S. Letters Pat. No. Letters 4,369,267 issued on Jan. 18, 1983 the specification for which is incorporated by reference herein;

(e) polystyrene as disclosed in U.S. Letters Pat. No. 4,369,227 issued on Jan. 18, 1983 the specification for which is incorporated by reference herein;

(f) polyene/α-olefin as exemplified and disclosed in U.S. Letters Pat. No. 4,369,291 the specification for which is incorporated by reference herein;

(g) poly-α-olefins disclosed in Canadian Letters Patent No. 1,137,069 issued on Dec. 7, 1982 the specification for which is incorporated by reference herein;

(h) polymeric compositions as disclosed in Canadian Letters Pat. No. 1,137,068 issued on Dec. 7, 1982 the specification for which is incorporated by reference herein;

(i) poly-α-olefins disclosed in Canadian Letters Patent No. 1,137,067 the specification for which is incorporated by reference herein;

(j) polyolefins described in Canadian Letters Patent No. 1,137,066 the specification for which is incorporated by reference herein;

(k) polyethylene oxides as disclosed in Canadian Letters Patent No. 1,137,065 issued on Dec. 7, 1982 the specification for which is incorporated by reference herein;

(l) olefin polymers and copolymers as disclosed in Canadian Letters Patent No. 1,139,737 issued on Jan. 18, 1983 the disclosure of which is incorporated by reference herein;

(m) polyolefins disclosed in Canadian Letters Patent No. 1,139,738 issued on Jan. 18, 1983 the disclosure of which is incorporated by reference herein;

(n) chlorinated PVC as disclosed in *Polymer* 1982, 23 (7, Suppl.), pages 1051–5, abstracted at *Chemical Abstracts*, Volume 97:14550y, 1982;

(o) polyepsilon caprolactone copolymers made by means of alcohol initiated polymerization as disclosed in *J.Polym.Sci.Polym.Chem.Ed.* 1982, 20(2), pages 319–26, abstracted at *Chemical Abstracts*, Volume 96:123625x, 1982;

(p) styrene acrylonitrile copolymers as disclosed in *Diss. Abstracts Int. B*, 1982, 42(8), page 3346 and abstracted at *Chemical Abstracts*, Volume 96:143770n, 1982;

(q) copolymers of epsilon caprolactone with 1,4-butane diol as disclosed in Kauch Rezine, 1982, (2), pages 8–9, abstracted at *Chemical Abstracts*, Volume 96:182506g, 1982;

(r) polyesters as disclosed in U.S. Letters Pat. No. 4,326,010 the specification for which is incorporated by reference herein;

(s) chlorinated polyethylene as disclosed by Belorgey, et al, *J.Polym.Sci.Plym.Ed.* 1982, 20(2), pages 191–203;

(t) plasticized polyepsilon caprolactone copolymers containing dimethyl phthalate plasticizers as set forth in Japanese Patent No. J81/147844, abstracted at *Chemical Abstracts*, Volume 96:669984y, 1982, the specification for which is incorporated by reference herein;

(u) maleic anhydride modified adducts of polyepsilon caprolactone polyols and ethylenically unsaturated monomer as disclosed in U.S. Letters Pat. No. 4,137,279 issued on Jan. 30, 1979 the specification for which is incorporated by reference herein;

(v) polyurethane polymers having lactone backbones as disclosed in U.S. Letters Pat. No. 4,156,067 issued on May 22, 1979 the disclosure of which is incorporated by reference herein;

(w) polyurethane polyether resins wherein the resin is obtained by reacting a polyfunctional lactone with a long chain polyalkylene diol and a urethane precursor as disclosed in U.S. Letters Pat. No. 4,355,550 issued on Mar. 10, 1981 the disclosure of which is incorporated by reference herein; and (x) resins having polyurethane backbones as disclosed in U.S. Letters Pat. No. 3,975,350 issued on Aug. 17, 1976 the disclosure of which is incorporated by reference herein.

Examples of poly(epsilon caprolactone) homopolymers as set forth, for example, in U.S. Letters Pat. No. 4,496,467 are those having the structures:

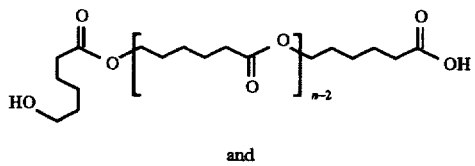

and

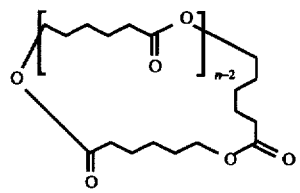

wherein n represents an integer of from about 500 up to about 1,200 with the proviso that the average "n" varies from about 600 up to about 800.

Downstream from the addition point of the dimethyl substituted oxymethyl cyclohexane derivative-containing compositions of our invention taken alone or taken together with other insect repellent agents and fragrance materials, optionally, the gaseous liquid containing blowing agent may be added (e.g., at "barrel segments" S-5, S-6, S-7, S-8, S-9 or S-10) using the polymer addition "barrel segment" as a reference "barrel segment" S-1. Examples of the gaseous blowing agents are carbon dioxide in proportions of from 1 up to 99% by volume nitrogen and from 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 to about 150 psig. Higher pressure may be used without adversely affecting the usefulness of the foamed insect repellent composition-containing particle.

The feed rate range of insect repellent compositions which contain but which are not limited to the dimethyl substituted oxymethyl cyclohexane derivative-containing compositions of our invention may be between about 0.5% up to about 45% by weight of the polymer. It must be emphasized at this point that the insect repellent composition of our invention which are the dimethyl substituted oxymethyl cyclohexane derivative-containing compositions of our invention are in and of themselves aromatizing materials. However, the maximum quantity of the combination of other aromatizing materials and the appropriate dimethyl substituted oxymethyl cyclohexane derivative-containing compositions of our invention is 45%.

The dies of the extruder may create rod, sheet, film or ribbon. The resulting product may then, if desired, be pelletized to form insect repellent composition-containing polymer particles or the ribbon may be used "as is" as an insect repellent-containing polymeric article of manufacture itself.

In addition to the optional gaseous blowing agents (which are necessarily "inert" gases), blowing agents may be added at the same point on the extruder which will create gaseous voids in the insect repellent-containing polymer articles of our invention and these "blowing agents" are well known to one having ordinary skill in the art. Examples of such non-gaseous containing materials which yield gases on admixture with the polymer in the extruder but which are still inert to the insect repellent (or attractant in the event of formulation of microporous polymeric particles containing the compound having the structure:

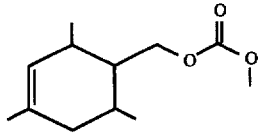

for use in insect traps as the case may be) are as follows:
(i) under high pressure, ethylene, methane, propane, butane, propylene, methyl chloride, methyl bromide, vinyl chloride and methylene dichloride as more specifically described in U.S. Letters Patent No. 2,387,730 the specification for which is incorporated by reference herein;
(ii) ordinarily liquid material such as n-pentane, isopentane, cyclopentane, hexane and petroleum ether fractions or halogen hydrocarbons such as $CFCL_3$, $CF_2CL_2$, $CH_3Cl$, $CH_2Cl_2$ separately or in admixture with one another as set forth in U.S. Letters Pat. No. 3,758,425, column 4, lines 1–5 the specification for which is incorporated by reference herein;
(iii) dichlorotetrafluoromethane, tetramethylmethane, monochlorodifluoromethane, dichlorodifluoromethane and dichlorotetrafluoromethane as described in U.S. Letters Pat. Nos. 2,948,664 and 2,948,665 issued on Aug. 9, 1990 the specifications for which are incorporated by reference herein; and
(iv) azo bis(formamide), diazoaminobenzene; N,N-dinitrosopentamethylene tetramine; N,N-dimethyl, N,N-dinitrosoterephthalamide; p,p'-oxy-bis-(benzene sulfonyl semicarbazide); aza bis(isobutyronitrile)p,p'-oxy-bis-(benzene sulfonyl hydrazide); p,p'-diphenyl-bis(sulfonyl hydrazide);

benzene-sulfonyl hydrazide; m-benzene-bis(sulfonyl hydrazide) as more specifically described in U.S. Letters Pat. No. 3,298,975 issued on Jan. 17, 1967 the specification for which is incorporated by reference herein.

The resulting extruded (and, if desired, pelletized) material may then be, for example, injection molded to form a useful article. Such injection molding can be carried out in accordance with the procedure as set forth in U.S. Letters Patent No. 3,268,636 issued on Aug. 23, 1966 the specification for which is incorporated by reference herein.

In addition, our invention relates to candle body materials which on use are both insect repellent and perfuming which contain the appropriate dimethyl substituted oxymethyl cyclohexane derivative-containing compositions of our invention and, if desired, other insect repellent materials including, for example, at least one of the compounds having the structure:

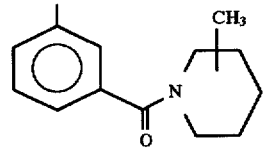

in order to repel houseflies (*Musca domestics L.* (Diptera:Muscidae)) and/or the mosquitoes, Aedes aegypti and or the insect species:
Culex nigripalpus;
Aedes atlanticus;
Culex salinarius;
Aedes vexans;
Culex spp.;
Simulium spp.;
Psoroferia ferox;
Aedes infirmatus;
Drosophila melanogaster;
Coccinellidae;
Anopheles crucians;
Psoroferia columbiae;
Culicoides spp.; and
Aedes spp.
and/or the horn fly, *Haematobia irritans* [L.].

The housefly, horn fly and mosquito-repellent-perfuming compositions which form part of the candle body materials are within the following specifications:
(i) from 5 up to 100% by weight of an efficacious perfuming/insect repellent composition containing an appropriate dimethyl substituted oxymethyl cyclohexane derivative-containing composition of our invention; and
(ii) from 0 up to 95% by weight of an additional standard perfuming substance (non-insect repellent or insect repellent) which may include but is not limited to:
1-nonen-3-ol;
1-octen-4-ol;
α-damascone;
β-damascone;
δ-damascone;
trans,trans δ-damascone;
methyl jasmonate;
dihydromethyl jasmonate;
the schiff base of vanillin and methyl anthranilate;
the schiff base of ethyl vanillin and methyl anthranilate;
vanillin; and
ethyl vanillin.

The foregoing formula may require a solubilizing agent, e.g., the methyl ester of dihydroabietic acid (commercial name: HERCOLYN® D), benzyl benzoate, isopropyl myristate and/or $C_{12}$–$C_{14}$ isoparaffin hydrocarbons.

The candle base composition can be standard paraffin wax, or it can be transparent or pastel shaded as more particularly described in U.S. Letters Pat. No. 3,615,289 issued on Oct. 26, 1971 (the disclosure of which is incorporated by reference herein) and wherein the candle body comprises as the basic components a mixture of:

(i) a thermoplastic polyamide resin formed from linoleic acid polymerized with a polyamine compound;

(ii) an alkanol amide or alkanol amine; and (iii) a stearic acid compound.

The weight ratio of candle body:insect repellent/perfumant substance or our invention may vary from about 0.8% up to about 10% with a range of from about 0.8% up to about 2.0% being preferred when no additional non-insect repelling perfume oil is used in conjunction with the appropriate dimethyl substituted oxymethyl cyclohexane derivative-containing composition of our invention; and with a range of from about 1.5% up to about 10% by weight of the overall composition being preferred when an additional non-insect repelling perfume oil is used in conjunction with the appropriate dimethyl substituted oxymethyl cyclohexane derivative-containing composition of our invention.

Specifically, the polyamide may be a VERSAMID® resin which is a thermoplastic condensation product of polymerized linoleic acid with various polyamine compounds such as ethylene diamine, ethylene triamine and the like. Specific VERSAMID® compounds are VERSAMID® 900, VERSAMID® 930, VERSAMID® 940, VERSAMID® 948, VERSAMID® 950 and VERSAMID® 1635. These compounds are products of the Henkel Chemical Corporation of Minneapolis, Minn.

Another substance required in the clear candle composition consists of about 20–55% by weight of an alkanol amine or alkanol amide prepared by the reaction of a fatty acid ester and amine whereby the ester and the amine are in substantially equal proportions, for example, compounds such as BARLOL® 12C2 (manufactured by the Baroid Chemical Company) a monoalkyl diethanolamine having 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. The stearic acid compounds serve as stabilizing agents which permit the ready incorporation of the insect repellent/perfumant compositions of our invention up to a level of approximately 5% (total proportion of perfume oil-insect repellent composition). They are carriers for the perfumant/insect repellent and may be used in a proportion of between 1 and 50% by weight of the composition although the preferable range is between 20 to 30%. In this connection, it is possible to use up to about 10% by weight of a perfumant/insect repellent if part of the formula is replaced by the material NEVEX® 100, a product which is a coumarin-indene copolymer resin of very little unsaturation manufactured by the Neville Chemical Company.

Rather than being a crystalline paraffin wax, the candle base of our invention may be an oil gel that has as its base a light mineral oil, an inexpensive natural oil or a combination of such oils which oil gel has a non-greasy surface and feel and sufficient rigidity to be self-supporting at room temperature. Such a gel is disclosed in U.S. Letters Pat. No. 3,645,705 issued on Feb. 29, 1972 the disclosure of which is incorporated by reference herein. Such compositions of matter include:

(a) from about 35% up to about 85% by weight of an oil which is normally liquid at room temperature chosen from the group consisting of light mineral oils and natural oils having iodine values substantially within the range of 40–135;

(b) from about 7% up to about 40% by weight of a long chain polyamide having a molecular weight substantially within the range of 6,000–9,000 and a softening point substantially within the range of 18° C.–48° C.; and (c) from about 7% up to about 30% of alcohol selected from the group consisting of 8 to 12 carbon primary alcohols.

The dimethyl substituted oxymethyl cyclohexane derivatives of our invention may be in the form of racemic mixtures or they may be in the form of sterioisomers. Thus, for example, representations of such sterioisomers are representations having the following structures:

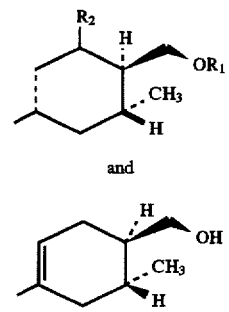

wherein $R_1$ is methyl or ethyl and $R_2$ is hydrogen or methyl.

DETAILED DESCRIPTION OF THE DRAWINGS

The data set forth in FIGS. 1A, 1B, 2A, 2B, 3, 4, 5, 6, 7, 8, 8A, 8B, 8C, 22 and 23 were determined using the olfactometer of FIG. 10 and the insect trap of FIG. 21.

Referring to the olfactometer of FIG. 10, said olfactometer is described in detail in U.S. Letters Pat. No. 5,118,711 issued on Jun. 2, 1992 the specification for which is incorporated by reference herein.

Referring to FIG. 10, air supply source 3634 provides air to mixing station 3636 wherein the air is mixed with treatment agent from treatment agent source 3635 (source of, for example, the repellent composition which is an appropriate dimethyl substituted oxymethyl cyclohexane derivative-containing composition). The resulting mixture passes through the tube 3636q and enters the apparatus through the side portals. The entry is through a spacer plate and above base plate 3625. The entry of the air-treatment agent is in a direction parallel to the surface of base plate 3625. Thus, the base plate 3625 is separated from spacer plate 3629 for the air-treatment agent (e.g., the appropriate dimethyl substituted oxymethyl cyclohexane derivative-containing composition of our invention).

Air exits through line 3533a using exhaust fan 3633. The air exit is indicated by reference numeral 3537.

Simultaneously, with the supplying of air and treatment agent from mixing station 3636, light is supplied from beneath the enclosed insect feeding and/or stimulating means through light guides 3652 from light source 3551 which is powered by electric power supply 3550 marketed by RADIO SHACK®, Division of Tandy Corporation of Forth Worth, Tex. 76102 under the Trademark ARCHER®, Catalog No. 276–228 ("1.0 mm optical plastic fiber length 5 meter"). An example of light source 3551 is KRATOS® Monochromator Illuminator GM 100 Miniature VIS-IR Grating Monochromator (Model No. GM 100-1, GM 100-2, GM 100-3 or GM 100-4) as manufactured by KRATOS® Analytical Instruments Corporation, 170 Williams Drive, Ramsey, N.J. 07446. Another light supply source is the KRATOS® GM 200 Double Grating Monochromator. Another example of a useful light source is the KRATOS® GM 252 High Intensity Grating Monochromator. The base plate 3625 is also separated from the spacer plate 3629 for the light guides 3652 whereby the light guides 3652 are held in place in the base plate 3625 whereby the light (or other forms of radiation) is directed in a direction perpendicular to the electrical sensor element 3610. Air supply source from location 3634 and treatment agent from location 3635 is mixed at mixing station 3636 whereupon treatment agent and air in admixture is passed through lines 3636a and 3636g through portals located in the spacer element 3628 in a direction along a directional vector parallel to the electrical sensing element 3610 held in place by holders 3610a and 3610b. The electrical sensing elements are located directly below the horizontally positioned insect feeding and/or stimulating microporous substantially planar lamina 3670 which is held in place by ring 3660 located on spacer plate 3629 spaced from the base plate 3625 by spacer ring 3628. It should be noted that the spacer plate 3629, spacer ring 3628 and base plate 3625 enclose the entire "enclosed insect feeding and/or stimulating means" which have controlled limited access to the external environment surrounding the apparatus and in which the insects to be tested, e.g., mosquitoes, horn flies or houseflies, are placed.

The insect attractant quantitative detecting means made up of wires 3699 (the entire grid being denoted using reference numeral 3610) is located immediately beneath the porous membrane 3670, the outer surface of which contains a feeding stimulant composition or stimulant composition for insects (for example, agar). Immersed in the feeding stimulate composition or stimulant composition for insects (e.g., agar) is electrode 3679 connected to wire 3619 which connects with either wire 3619a or 3619b which is connected to the grid wires 3699 (which make up the insect attractant quantitative detecting means located immediately below lamina 3670).

As stated, supra; the sensor causes an electrical impulse caused by the pressure of the insects landing to proceed through wires 3619a and 3619b to an electrically biased differential amplifier 3639 (using electrical power supply 3539) also connected to wire 3619c which is connected to the electrode 3679 which is immersed in the feeding stimulant composition or stimulant for the insect and then to a multi-channel A.C. converter 3523. Converter 3523 is associated with program tape storage 3524, printer 3520 and data link to digital computer 3521. Differential amplifier 3639 is connected in series to electrical bias for pseudo host 3669 which in turn is connected to wire 3619 which in turn is connected to the electrode 3679 immersed in the insect stimulant composition located on the surface of porous lamina 3670.

Referring to the testing apparatus, the semiochemical field trap 1000 for blood feeding arthropods, field trap 1000 is located in a three-space with axes perpendicular to one another. The semiochemical field trap 1000 is shown in perspective view in FIG. 21 comprising:

(1) an upright, vertically disposed housing;
(2) extending outwardly from the housing a plurality of horizontally disposed hollow housings 116a and 116b which have contained therein insect sticky traps;
(3) air 138 and/or carbon dioxide supply means 134 and 136 for supplying air and/or carbon dioxide into the vertical hollow housing and then through the plurality of horizontally disposed hollow housings 116a and 116b; and
(4) at least one power supply means for energizing radiation means located on the vertical hollow housing whereby on engagement of the power supply means with the radiation means and operation of the air 138 and/or carbon dioxide supply means 134 and 136, arthropods in the vicinity of the trap are attracted by the activated radiation means and the gas emanating from the horizontally disposed hollow housing 116a to a location so close to the trap 1000 that in the event that an attracting semiochemical located in the housings of 116a and 116b is detected by at least one of the arthropods, at least one of the arthropods will enter the inner void of the horizontally disposed hollow housings 116a and 116b counter current the gas stream emanating therefrom and remain permanently entrapped therein.

The semiochemical field trap 1000 of FIG. 21 is disclosed in detail in U.S. Letters Pat. No. 5,228,233 issued on Jul. 20, 1993, the specification for which is incorporated by reference herein.

FIG. 1A is a series of graphs depicted in three dimensions (in a rectangular mode for the "X" and "Y" axes) showing the relative attractiveness or repellency of air, ISOCYCLOGERANIOL having the structure:

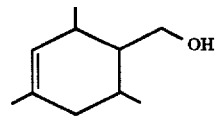

and FLORALOL having the structure:

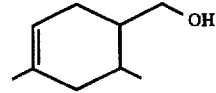

with respect to the attractiveness or repellency of the mosquito, Aedes aegypti. The graph indicated by reference numeral 150a is for air. The graph indicated by reference numeral 145a is for ISOCYCLOGERANIOL. The graph indicated by reference numeral 176a is for FLORALOL. The "X" axis along which the particular materials are measured insofar as their attractiveness or repellency is concerned is indicated by reference numeral 107. The number of insects collected per interval is indicated on the "Y" axis and the "Y" axis is indicated by reference numeral 100. The results are tabulated in Table I(A) as follows:

TABLE I(A)

| Composition Tested | Graph No. | Insects Collected per Interval | | | | | |
|---|---|---|---|---|---|---|---|
| ISOCYCLO-GERANIOL | 145a | 4 | 1 | 0 | 0 | 0 | 3 |
| Air | 150a | 555 | 512 | 552 | 552 | 574 | 494 |
| FLORALOL | 176a | 3 | 1 | 0 | 0 | 0 | 0 |

FIG. 1B is a series of graphs depicted in three dimensions (in a rectangular mode for the "X" and "Y" axes) showing the relative attractiveness or repellency of air, ISOCYLCOGERANIOL and FLORALOL with reference to attractiveness or repellency for Aedes aegypti. The graphs are based on experiments run for a period of six hours with six intervals of one hour each. The graph indicated by reference numeral 145b is for ISOCYLCOGERANIOL. The graph indicated by reference numeral 150b is for air. The graph indicated by reference numeral 176b is for FLORALOL. The results are tabulated in Table I(B) as follows:

TABLE I(B)

| Composition Tested | Graph No. | Insects Collected per Interval | | | | | |
|---|---|---|---|---|---|---|---|
| ISOCYCLO-GERANIOL | 145b | 3 | 0 | 2 | 5 | 4 | 0 |
| Air | 150b | 494 | 547 | 580 | 566 | 559 | 533 |
| FLORALOL | 176b | 0 | 5 | 1 | 4 | 2 | 0 |

FIG. 2A is a series of graphs depicted in three dimensions (in a rectangular mode for the "X" and "Y" axes) showing the relative attractiveness or repellency of the materials:

(i) air;

(ii) ISOCYLCOGERANIOL having the structure:

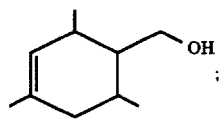

(iii) FLORALATE having the structure:

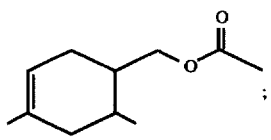

(iv) DIHYDROFLORALOL having the structure:

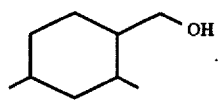

The test data is for the mosquitoes, Aedes aegypti. The graphs are based on experiments run for a period of one hour with six intervals of ten minutes each. The graph indicated by reference numeral 200a is for air. The graph indicated by reference numeral 205a is for ISOCYCLOGERANIOL. The graph indicated by reference numeral 203a is for FLORALATE. The graph indicated by reference numeral 202a is for DIHYDROFLORALOL. The results are tabulated in Table II(A) as follows:

TABLE II(A)

| Composition Tested | Graph No. | Insects Collected per Interval | | | | | |
|---|---|---|---|---|---|---|---|
| Air | 200a | 393 | 494 | 570 | 554 | 584 | 578 |
| ISOCYCLO-GERANIOL | 205a | 0 | 0 | 0 | 0 | 0 | 0 |
| FLORALATE | 203a | 1 | 22 | 0 | 24 | 7 | 27 |
| DIHYDRO-FLORALOL | 202a | 0 | 0 | 0 | 0 | 0 | 0 |

FIG. 2B is a series of graphs depicted in three dimensions (in a rectangular mode for the "X" and "Y" axes) showing the relative attractiveness or repellency of the materials:

(i) air;

(ii) ISOCYLCOGERANIOL having the structure:

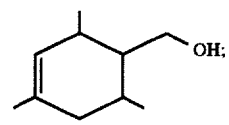

(iii) FLORALATE having the structure:

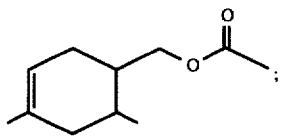

(iv) DIHYDROFLORALOL having the structure:

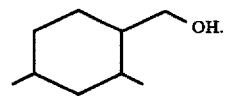

The graphs are based on experiments run for a period of 18 hours with six intervals of 3 hours each using as the insect to be tested the mosquito, Aedes aegypti. The graph indicated by reference numeral 200b is for air. The graph indicated by reference numeral 205b is for ISOCYCLOGERANIOL. The graph indicated by reference numeral 203b is for FLORALATE. The graph indicated by reference numeral 202b is for DIHYDROFLORALOL. The results are tabulated in Table II(B) as follows:

TABLE II(B)

| Composition Tested | Graph No. | Insects Collected per Interval | | | | | |
|---|---|---|---|---|---|---|---|
| Air | 200b | 4,472 | 3,833 | 5,026 | 4,108 | 716 | 0 |
| ISOCYCLO-GERANIOL | 205b | 7 | 6 | 50 | 134 | 0 | 0 |
| FLORALATE | 203b | 19 | 7 | 0 | 0 | 0 | 0 |
| DIHYDRO-FLORALOL | 202b | 1 | 2 | 0 | 1 | 0 | 0 |

FIG. 3 is a series of graphs depicted in three dimensions (in a rectangular mode for the "X" and "Y" axes) showing the relative attractiveness or repellency of the materials:

(i) air; and (ii) DIHYDROFLORALOL having the structure:

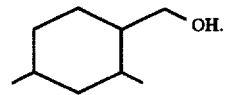

The graphs are based on experiments run for a period of one hour with six intervals of ten minutes each using as the insect to be tested the horn fly (Haematobia irritans [L.]). The graph indicated by reference numeral 300 is for air. The graph indicated by reference numeral 302 is for DIHYDROFLORALOL. The results are tabulated in Table III as follows:

TABLE III

| Composition Tested | Graph No. | Insects Collected per Interval | | | | | |
|---|---|---|---|---|---|---|---|
| Air | 300 | 171 | 302 | 257 | 260 | 281 | 164 |
| DIHYDRO-FLORALOL | 302 | 22 | 3 | 23 | 1 | 0 | 1 |

FIG. 4 is a series of graphs depicted in three dimensions (in a rectangular mode for the "X" and "Y" axes) showing the relative attractiveness or repellency of the materials:

(i) air;

(ii) ISOCYLCOGERANIOL having the structure:

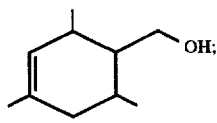

(iii) FLORALATE having the structure:

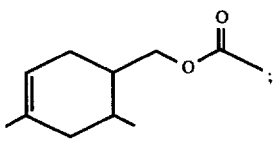

(iv) FLORALOL having the structure:

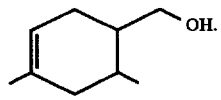

The graphs are based on experiments run for a period of one hour with six intervals of ten minutes each using as the insect to be tested the horn fly (*Haematobia irritans* [L.]). The graph indicated by reference numeral 400 is for air. The graph indicated by reference numeral 445 is for ISOCYCLOGERANIOL. The graph indicated by reference numeral 443 is for FLORALATE. The graph indicated by reference numeral 426 is for FLORALOL. The results are tabulated in Table IV as follows:

TABLE IV

| Composition Tested | Graph No. | Insects Collected per Interval | | | | | |
|---|---|---|---|---|---|---|---|
| Air | 400 | 170 | 198 | 304 | 339 | 229 | 346 |
| ISOCYCLO-GERANIOL | 445 | 0 | 0 | 0 | 0 | 0 | 0 |
| FLORALATE | 443 | 1 | 5 | 0 | 0 | 1 | 0 |
| FLORALOL | 426 | 0 | 0 | 0 | 0 | 0 | 0 |

FIG. 5 is a series of graphs depicted in three dimensions (in a rectangular mode for the "X" and "Y" axes) showing the relative attractiveness or repellency of the materials:

(i) air;

(ii) CAMEKOL DH having the structure:

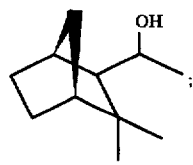

(iii) FLORALOL having the structure:

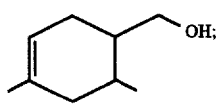

(iv) DIHYDROFLORALOL having the structure:

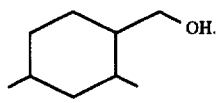

The graphs are based on experiments run for a period of one hour with six intervals of ten minutes each using as the insect to be tested the horn fly (*Haematobia irritans* [L.]). The graph indicated by reference numeral 500 is for air. The graph indicated by reference numeral 536 is for CAMEKOL DH. The graph indicated by reference numeral 526 is for FLORALOL. The graph indicated by reference numeral 542 is for DIHYDROFLORALOL. The results are tabulated in Table V as follows:

TABLE V

| Composition Tested | Graph No. | Insects Collected per Interval | | | | | |
|---|---|---|---|---|---|---|---|
| Air | 500 | 1 | 5 | 73 | 170 | 43 | 8 |
| CAMEKOL DH | 536 | 1 | 1 | 0 | 0 | 1 | 0 |
| FLORALOL | 526 | 4 | 1 | 1 | 0 | 0 | 0 |
| DIHYDROFLORALOL | 542 | 0 | 6 | 0 | 1 | 0 | 0 |

FIG. 6 is a series of graphs depicted in three dimensions (in a rectangular mode for the "X" and "Y" axes) showing the relative attractiveness or repellency of the materials:

(i) air;

(ii) FLORALATE having the structure:

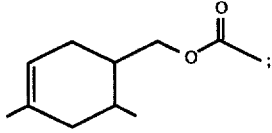

(iii) DIHYDROFLORALOL having the structure:

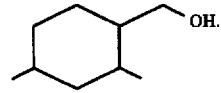

The graphs are based on experiments run for a period of one hour with six intervals of ten minutes each using as the insect to be tested the horn fly (*Haematobia irritans* [L.]). The graph indicated by reference numeral 600 is for air. The graph indicated by reference numeral 643 is for FLORALATE. The graph indicated by reference numeral 642 is for DIHYDROFLORALOL. The results are tabulated in Table VI as follows:

TABLE VI

| Composition Tested | Graph No. | Insects Collected per Interval | | | | | |
|---|---|---|---|---|---|---|---|
| Air | 600 | 0 | 62 | 1 | 1 | 1 | 19 |
| FLORALATE | 643 | 0 | 3 | 0 | 0 | 0 | 2 |
| DIHYDROFLORALOL | 642 | 0 | 6 | 3 | 0 | 2 | 7 |

FIG. 7 is a series of graphs depicted in three dimensions (in a rectangular mode for the "X" and "Y" axes) showing the relative attractiveness or repellency of the materials:
(i) air; and
(ii) FLORALOL having the structure:

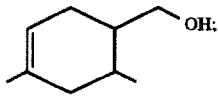

The graphs are based on experiments run for a period of one hour with six intervals of ten minutes each using as the insect to be tested the housefly, Musca domestica L. (Diptera:Muscidae). The graph indicated by reference numeral 700 is for air. The graph indicated by reference numeral 726 is for FLORALOL. The results are tabulated in Table VII as follows:

TABLE VII

| Composition Tested | Graph No. | Insects Collected per Interval | | | | | |
|---|---|---|---|---|---|---|---|
| Air | 700 | 172 | 17 | 0 | 2 | 0 | 0 |
| FLORALOL | 726 | 2 | 8 | 0 | 3 | 0 | 0 |

FIG. 8A is a graph showing the mean number of mosquitoes collected (on the "Y" axis) versus the treatment substance (on the "X" axis) using the field trap of FIG. 21 having six ports and three infrared light emitting diodes and using the following materials:
(i) a 50:50 mole:mole mixture of air and carbon dioxide with the feed rate of carbon dioxide being 2.7 gram moles per hour;
(ii) CAMEKOL DH having the structure:

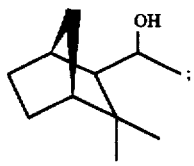

(iii) ISOCYCLOGERANIOL having the structure:

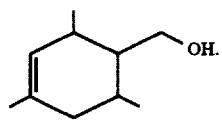

The bar graph showing the mean number of insects collected using the mixture of air and carbon dioxide is indicated by reference numeral 8000a. The bar graph indicating the mean number of mosquitoes collected using CAMEKOL DH is indicated by reference numeral 8036a. The bar graph using ISOCYCLOGERANIOL is indicated by reference numeral 8045a.

FIG. 8B is a series of bar graphs showing the mean number of mosquitoes collected on the "Y" axis versus the treatment substance on the "X" axis using the semiochemical field trap of FIG. 21 having six ports with three infrared light emitting diodes. The substances used are:
(i) a 50:50 mole:mole mixture of air and carbon dioxide with the feed rate of carbon dioxide being 2.7 gram moles per hour;
(ii) DIHYDROFLORALOL having the structure:

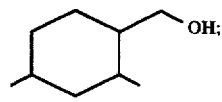

(iii) ISOCYCLOGERANIOL having the structure:

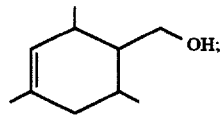

(iv) ISOCYCLOGERANIOL methyl carbonate having the structure:

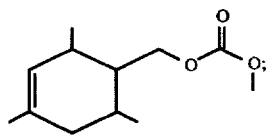

(v) ISOCYCLOGERANIOL ethyl carbonate having the structure:

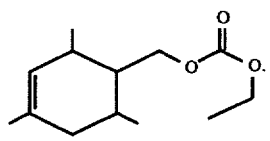

The bar graph showing the mean number of mosquitoes collected using the mixture of air and carbon dioxide is indicated by reference numeral 8000b. The bar graph using DIHYDROFLORALOL is indicated by reference numeral 8042b. The bar graph showing the results using ISOCYCLOGERANIOL is indicated by reference numeral 8045b. The bar graph showing the results when using ISOCYCLOGERANIOL methyl carbonate is indicated by reference numeral 8003b. The bar graph showing the results using ISOCYCLOGERANIOL ethyl carbonate is indicated by reference numeral 8004b.

FIG. 8C is a series of bar graphs indicating the mean number of mosquitoes trapped on the "Y" axis versus the treatment substance on the "X" axis using a semiochemical field trap as illustrated in FIG. 21 having six ports with three infrared light emitting diodes using the following substances:
(i) a mixture of air and carbon dioxide in a mole ratio of 50:50 at a rate of carbon dioxide of 2.7 gram moles per hour;

(ii) FLORALOL having the structure:

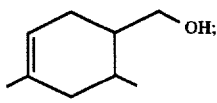

(iii) FLORALATE having the structure:

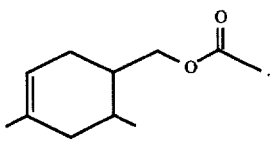

The bar graph showing the results using the mixture of air and carbon dioxide is indicated by reference numeral 8000c. The bar graph showing the results using FLORALOL is indicated by reference numeral 8026c. The bar graph showing the results using FLORALATE is indicated by reference numeral 8043c.

In each of the experiments, the results for which are shown in FIGS. 8A, 8B and 8C, the following insects were shown to be either repelled or attracted:

Culex nigripalpus;

Aedes atlanticus;

Culex salinarius;

Aedes vexans;

Culex spp.;

Simulium spp.;

Psoroferia ferox;

Aedes infirmatus;

Drosophila melanogaster;

Coccinellidae;

Anopheles crucians;

Psoroferia columbiae;

Culicoides spp.; and

Aedes spp.

In referring to the extruder of FIG. 9, polymer 12 and 13 is admixed in vessel 14 and added at barrel segment S-1 of barrel 16 to the extruder which is powered by motor 15 held in place by bracket 23A. Simultaneously, into barrel segment S-6 (one of segments 18a, 18b, 18c or 18d) is added the insect repellent which is one or more of the dimethyl substituted oxymethyl cyclohexane derivative-containing compositions of our invention previously held in container 17. The repellent/perfumant mixture is pumped through pump 23 into barrel segment 18c/S-6. Simultaneously, foaming agent is added from vessel 19 into barrel segment S-8 from barrel segment S-10, a foamed tow containing polymer having imbedded therein insect repellent/perfume is passed through cooling bath 20 and the cooled tow 22 is then passed into mascerating machine 21 wherein the tow is chopped into particles and held in container 21a for future use, e.g., for use in conjunction with the manufacture of the insect repellent soap or detergent bars described in detail, infra.

Referring to FIGS. 11–20, inclusive, a preferred embodiment of our invention comprises an ellipsoidally-shaped detergent tablet 830. A preferred embodiment of our invention comprises an ellipsoidally-shaped detergent tablet 830 containing a solid plastic core 832 which can be fabricated from, for example, polyethylene, polypropylene, nylon, a biodegradable polymer such as poly(epsilon caprolactone) or any polymer capable of having therein microvoids from which an insect repelling/perfuming substance, e.g., at least on of the appropriate dimethyl substituted oxymethyl cyclohexane derivative-containing compositions of our invention will be controllably transported from the plastic core into and through the soap cake over a reasonable period of time during the use of the soap cake. Such polymers can be microporous polymers, such as those described in U.S. Letters Pat. No. 4,247,498 issued on Jan. 27, 1981 the specification for which is incorporated herein by reference. Surrounding the central plastic core containing insect repellent 832, is detergent 830' which is in the solid phase at ambient conditions, e.g., room temperature and atmospheric pressure. Examples of workable detergents 830' are "elastic" detergents such as those described in U.S. Letters Pat. No. 4,181,632 issued on Jan. 1, 1980 the disclosure of which is incorporated herein by reference, or "transparent" soaps such as those set forth in U.S. Letters Pat. No. 4,165,293 issued on Aug. 21, 1979 the disclosure of which is incorporated herein by reference. Other examples of the detergent 830' useful in our invention are those set forth as "variegated soaps" in Canadian Letters Pat. No. 1,101,165 issued on May 19, 1981.

On use of the soap tablet 830 or detergent bar, the insect repellent agent originally located in plastic core 832 is transported at a steady state from core 832 through core surface 831 through the detergent 830' and finally through the surface of the detergent bar at, for example, 833, 834, 835 and 836.

The detergent bar or tablet 830 of our invention may be of any geometric shape, for example, a rectangular parallelepiped tablet as shown in FIGS. 15, 16 and 17 containing solid plastic core 839. The insect repellent located in solid plastic core 839 on use of the detergent bar passes through at steady state, surface 837 of FIG. 16, detergent 838 and finally surface 839 at, for example, locations 840, 841, 842 and 843. The environment surrounding the detergent bar on use thereof is then treated with the insect repellent at 843, 844 and 845, for example. Optionally, aromatizing agent can also be contained in the detergent bar (if desired) and so the environment surrounding the detergent bar on use thereof would also be aesthetically aromatized at 843, 844 and 845, for example, if the appropriate dimethyl substituted oxymethyl cyclohexane derivative-containing composition of our invention is insufficient for such aromatization. In certain instances, such appropriate dimethyl substituted oxymethyl cyclohexane derivative-containing compositions are indeed sufficient for such aromatization.

As is shown in FIGS. 18, 19 and 20, the plastic core of the detergent tablet 830 may have a single finite void at its center 851 (of FIGS. 19 and 20) in which the insect repellent agent and, optionally, any additional aromatizing agents are contained. The plastic core is a shell 848 having outer surface 852 (shown in FIGS. 19 and 20). The insect repellent agent (and, optionally, any additional aromatizing agent) contained in the void in the plastic core permeates through shell 848, past surface 852 at a steady state, through the detergent 847 and to the environment at, for example, 856, 857, 858 and 859.

In addition to the insect repellent contained in the core, e.g., core 839 or core void, the core can also contain other materials for therapeutic use, for example, bacteriastats, deodorizing agents and the like which are compatible with appropriate dimethyl substituted oxymethyl cyclohexane derivative-containing compositions of our invention. In the alternative, the plastic core of the detergent tablet of FIGS. 18, 19 and 20 may have an empty single finite void at its center 851 with the insect repellent contained in the shell 848.

At the end of the use of the detergent tablet, the hollow core or the solid core can be used as an insect imparting and aroma imparting or air freshener household article. In addition, depending on the ratio of the volume of the void 851 to the solid part of the detergent tablet of FIGS. 18, 19 and 20, the detergent tablet of FIGS. 18, 19 and 20 can be so fabricated that it will float on the surface of the liquid in which it is being used and this physical attribute has certain obvious advantages.

FIG. 22 is a series of bar graphs showing the feeding contact for a mean feeding for a mean feeding contact for a mean one hour feeding contact period of time using the olfactometer apparatus of FIG. 10. The number of feeding contacts are set forth on the "Y" axis and the treatment substance is set forth on the "X" axis. The bar graph indicated by reference numeral 2200 is for air and shows the results using said air. The bar graph indicated by reference numeral 2243 shows the results using FLORALATE having the structure:

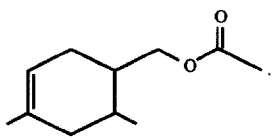

The bar graph indicated by reference numeral 2244 shows the results using geranial having the structure:

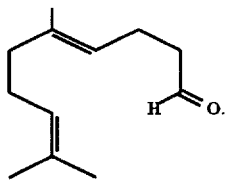

FIG. 23 is a series of bar graphs showing on the "Y" axis the mean 2–6 hour number of feeding contacts for the mosquitoes, Aedes aegypti, using the olfactometer of FIG. 10 versus the treatment substance on the "X" axis. The graph indicated by reference numeral 2300 is the graph showing the results using air. The graph indicated by reference numeral 2343 is the bar graph showing the results using FLORALATE having the structure:

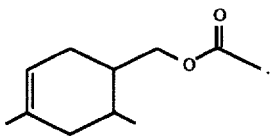

The graph indicated by reference number 2344 is the bar graph showing the results of this experiment using geranial having the structure:

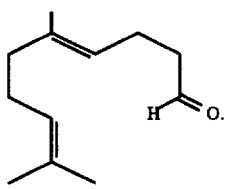

The apparatus of FIG. 10 is disclosed in detail in U.S. Letters Pat. No. 5,134,892 the specification for which is incorporated herein by reference.

The following examples are illustrative and the instant Patent Application is intended to be restricted only to the scope of the claims and not to the examples.

EXAMPLE I

A transparent candle base mixture is produced by intimately admixing the following ingredients:

| Ingredients | Parts by weight |
| --- | --- |
| VERSAMID ® 1635 | 34.0 |
| Barlol 12C2 | 51.0 |
| Butyl Stearate | 3.5 |
| NEVEX ® 100 | 5.0 |
| SPAN ® | 1.5 |
| Isopropyl Istostearate | 4.0 |
| Isopropyl Myristate | 4.0 |

The foregoing mixture is placed in an autoclave and intimately admixed with 22% by weight of the entire mixture of a perfuming-insect repellent composition containing the following ingredients:

| Ingredients | Parts by Weight |
| --- | --- |
| ISOCYCLOGERANIOL having the structure: | 25 |
| FLORALATE having the structure: | 25 |
| Geranial having the structure: | 25 |
| CAMEKOL DH having the structure: | 25 |

The autoclave is sealed and heated to 180° C. under 25 atmospheres pressure and maintained with vigorous shaking for a period of 5 hours. At the end of the 5 hour period, the autoclave is depressurized (being under a nitrogen pressure atmosphere) and the autoclave is opened and the contents are then poured into cylindrical candle molds 4" in height and 2" in diameter containing 0.125" wicks. The resulting candles have efficacious Aedes aegypti, Aedes albopictus and Musca domestics L. repellencies and have aesthetically pleasing aromas on use.

The candles are effective in preventing houseflies and the mosquito species Aedes aegypti and Aedes albopictus from entering a room in which four candles have been burning for 15 minutes, the said room having dimensions of 6'×15'×15' and having a 2'×2' open portal adjacent to a housefly and mosquito-infested region in the month of Aug. 1992 in the temperate zone of Highlands, N.J. adjacent Raritan Bay.

EXAMPLE II

A study was conducted to evaluate the efficacy of candles which are designated as "A", "B" and "C" in repelling houseflies (*Musca domestica* L. (Diptera:Muscidae)) and the mosquito species *Aedes aegypti* and *Aedes albopictus*.

Candle "A" contained 95% paraffin wax and 5% of ISOCYCLOGERANIOL ethyl carbonate having the structure:

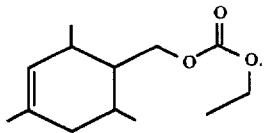

Candle "B" contained 90% paraffin wax and 10% citronella oil.

Candle "C" contained only paraffin wax.

The candles are allowed to burn for 20 minutes and the number of houseflies (*Musca domestica* L. (Diptera:Muscidae)) and mosquitoes (*Aedes aegypti* and *Aedes albopictus*) repelled is recorded for the next 60 minutes with the following equipment and procedure:

MATERIALS

Test Chamber

The evaluation was conducted in a 28.3 cubic meter chamber with airing ports. A screened cage measuring 15 cm×15 cm×47.5 cm was attached inside an upper airing port, and a screened repellency observation cage measuring 15 cm×15 cm×32.5 cm was attached outside the upper airing port. The two cages were held together by a Masonite plate which fit firmly in the airing port. A 4 cm hole located in the center of each Masonite plate provided an escape for the test insects. A barrier was used to close the hole.

Attractant

A caged grey mouse was used as an attractant and was placed inside the chamber in the larger section of the repellency cage.

Test Insects (i) Adult houseflies (*Musca domestica* L. (Diptera:Muscidae));

(ii) *Aedes aegypti* mosquitoes; and (iii) *Aedes albopictus* mosquitoes are test insects.

PROCEDURE

For each replicate, 75 to 100 adult houseflies (*Musca domestica* L. (Diptera:Muscidae)), 75 to 100 *Aedes aegypti* mosquitoes and 75 to 100 *Aedes albopictus* mosquitoes were removed from the rearing cage by means of a vacuum aspirator and transferred by carbon dioxide anesthesia to the inner cage containing the grey mouse. The assembled cage was placed in one of the upper ventilation ports of the chamber. For each experimental situation, the test insects were transferred to a clean cage containing the mouse. A candle containing the insect repellent substance to be tested was placed centrally on the chamber floor and burned for 20 minutes before initiating the repellency counts. The maximum period for the repellency counts was 60 minutes. The first repellency count was made at 10 minutes after the burning ended and subsequent counts were taken at 5-minute intervals thereafter. The number of houseflies (*Musca domestica* L. (Diptera:Muscidae)), *Aedes aegypti* mosquitoes and *Aedes albopictus* mosquitoes repelled were those escaping to the outside cage. For the control, counts were made in a similar manner, but no candle was burned.

The same three candles were used for all four replicates. Between replicates, the chamber was exhausted, the Kraft paper flooring for the chamber was replaced and the two screened repellency cages were submerged in hot detergent water, rinsed and dried.

RESULTS

The overall average percent of houseflies (*Musca domestica* L. (Diptera:Muscidae)), *Aedes aegypti* mosquitoes and *Aedes albopictus* mosquitoes repelled for each candle for 60 minutes was as follows:

Candle "A"—98%;

Candle "B"—52%; and

Candle "C"—12%.

The repellency against the three species:

*Musca domestics* L. (Diptera:Muscidae);

*Aedes aegypti*; and

*Aedes albopictus* were equivalent in this test.

What is claimed is:

1. A method of repelling at least one member of the insect species: *Musca domestics* L. (Diptera:Muscidae), *Aedes aegypti*, *Culex nigripalpus*; *Aedes atlanticus*; *Culex salinarius*; *Aedes vexans*; *Culex spp.*; *Simulium spp.*; *Psoroferia ferox*; *Aedes infirmatus*; *Drosophila melanogaster*; Coccinellidae; *Anopheles crucians*; *Psoroferia columbiae*; *Culicoides spp.*; *Aedes spp.*, and/or *Haematobia irritans* , and/or *Aedes albopictus* for a finite period of time from a three-dimensional space inhabited by said insect species member consisting essentially of the step of exposing said three-dimensional space to an effective insect species member-repelling concentration and quantity of the compound having the structure:

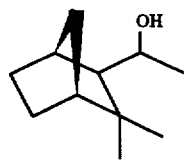

2. The method of claim 1 wherein the insect repelling substance is contained in a polymer matrix.

3. The method of claim 2 wherein the polymer matrix comprises a biodegradable polymer.

4. The method of claim 3 wherein the biodegradable polymer is a polycaprolactone polymer or a polyurethane polymer.

5. The method of claim 1 wherein the insect-repelling composition is initially admixed with a soap base; the resulting mixture is formulated into a soap article; and the resulting soap article is used in a washing machine in a washing procedure.

6. The method of claim 5 wherein the polymer matrix containing the insect repellant-containing composition is formed into a core and the core is surrounded with a soap base; and the resulting article is applied in a washing procedure to a person thereby causing insects to be repelled from said person immediately after said washing procedure is carried out.

* * * * *